(12) United States Patent
Farwick et al.

(10) Patent No.: US 6,822,085 B2
(45) Date of Patent: Nov. 23, 2004

(54) NUCLEOTIDE SEQUENCES WHICH CODE FOR THE CYSD, CYSN, CYSK, CYSE AND CYSH GENES

(75) Inventors: Mike Farwick, Bielefeld (DE); Klaus Huthmacher, Gelnhausen (DE); Natalie Schischka, Bielefeld (DE); Brigitte Bathe, Salzkotten (DE); Walter Pfefferle, Halle (DE); Michael Binder, Steinhagen (DE); Dieter Greissinger, Niddatal (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 59 days.

(21) Appl. No.: 09/962,357

(22) Filed: Sep. 26, 2001

(65) Prior Publication Data

US 2002/0086373 A1 Jul. 4, 2002

Related U.S. Application Data

(60) Provisional application No. 60/294,223, filed on May 31, 2001.

(30) Foreign Application Priority Data

| Sep. 30, 2000 | (DE) | 100 48 603 |
| Feb. 28, 2001 | (DE) | 101 09 691 |
| Jul. 28, 2001 | (DE) | 101 36 986 |

(51) Int. Cl.[7] .............................................. C07H 21/04
(52) U.S. Cl. .................... 536/23.7; 536/23.1; 536/23.2; 536/24.32; 435/6; 435/320.1
(58) Field of Search ................. 435/6, 320.1; 536/23.7, 536/23.1, 23.2, 24.32

(56) References Cited

FOREIGN PATENT DOCUMENTS

| EP | 1 108 790 | 6/2001 |
| WO | WO 97/15673 | 5/1997 |
| WO | 010842 | * 1/2001 |
| WO | WO 01/00842 | 1/2001 |
| WO | WO 01/00843 | 1/2001 |

OTHER PUBLICATIONS

Redenbach et al. Gencore Accession No. AL59708. 1996.*
Sherman et al. Gencore Accession No. AAC55842.*
Y. Q. Mao, et al., Database EBI Online, AC BI 'Online!' EMBL, MMCV_Strala, AC Q9X5UO, XP–002191266, 1 page, "Molecular Characterization and Analysis of the Biosynthetic Gene Cluster for the Antitumor Antibiotic Mitomycin C from Streptomyces Lavendulae NRRL 2564", May 30, 2000.

* cited by examiner

Primary Examiner—Jennifer Graser
(74) Attorney, Agent, or Firm—Oblon, Spivak, McClelland, Maier & Neustadt, P.C.

(57) ABSTRACT

Nucleotide sequences from coryneform bacteria which code for the cysD, cysN, cysK, cysE and cysH genes and a process for the fermentative preparation of amino acids using bacteria in which the genes mentioned are enhanced, a process for the fermentative preparation of L-amino acids using coryneform bacteria in which at least the cysD gene, the cysN gene, the cysK gene, the cysE gene and/or the cysH gene is present in enhanced form, and the use of polynucleotides which contain the sequences according to the invention as hybridization probes and a process for the preparation of an L-methionine-containing animal feedstuffs additive from fermentation broths.

21 Claims, 5 Drawing Sheets

Figure 1: Plasmid pEC-XK99E
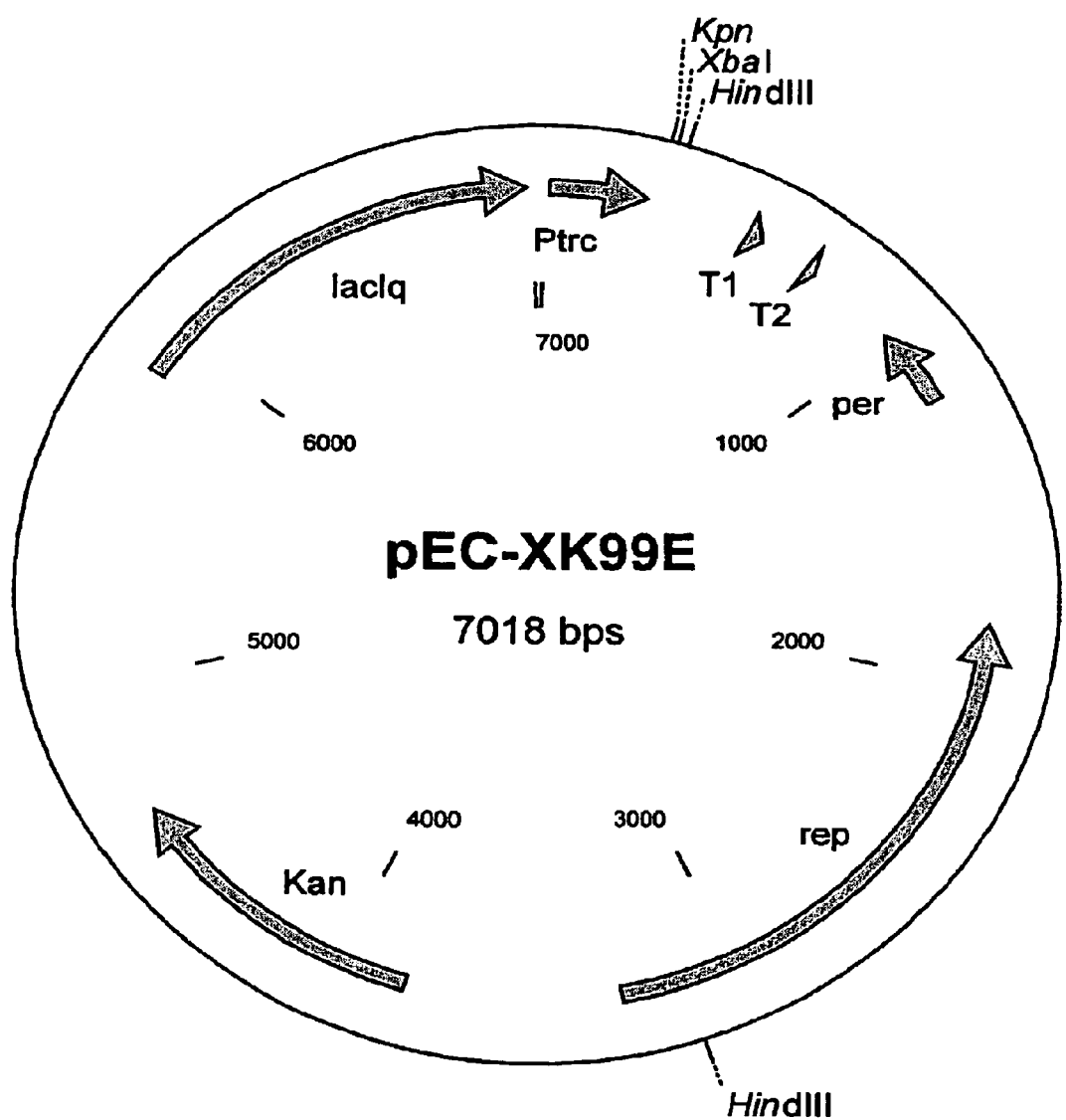

Figure 2: Plasmid pEC-XK99EcysDa1ex
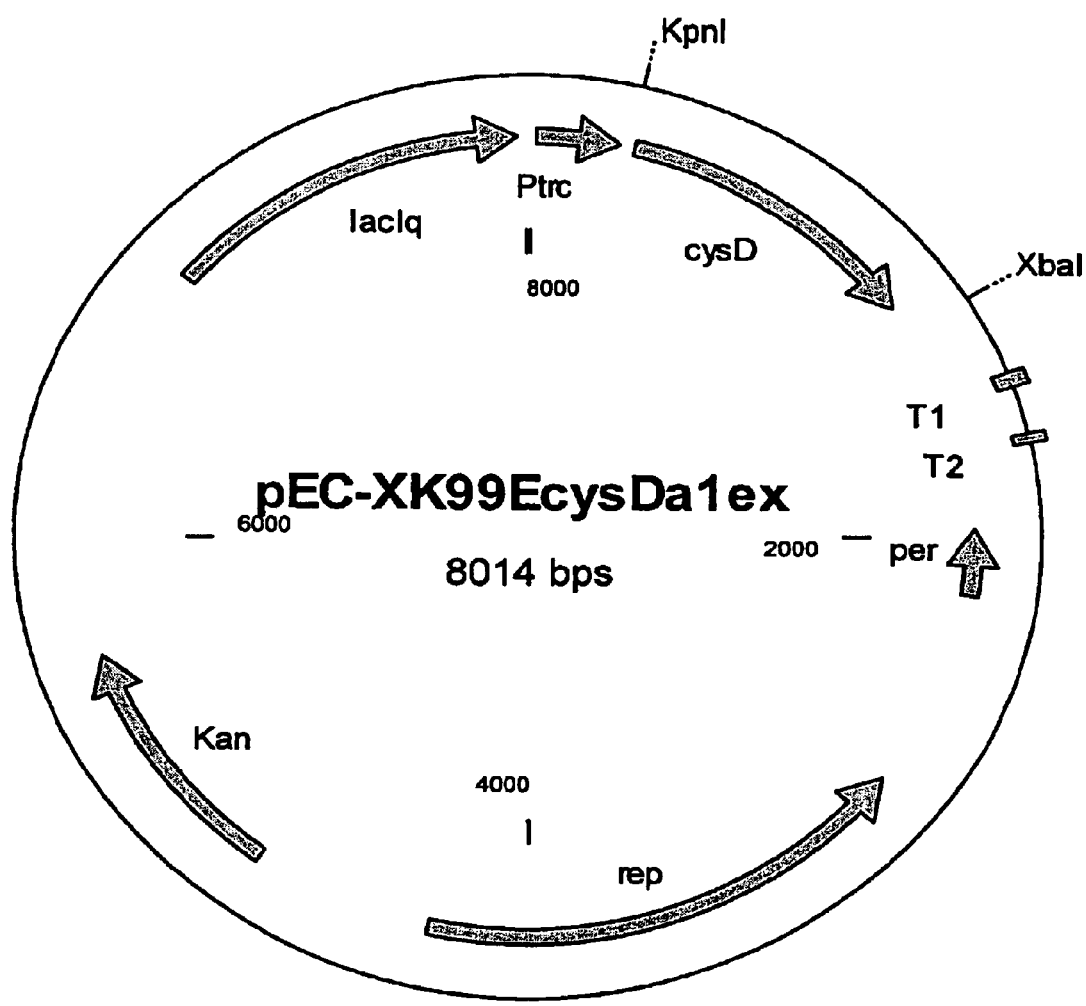

Figure 3: Plasmid pEX-XK99EcysKalex
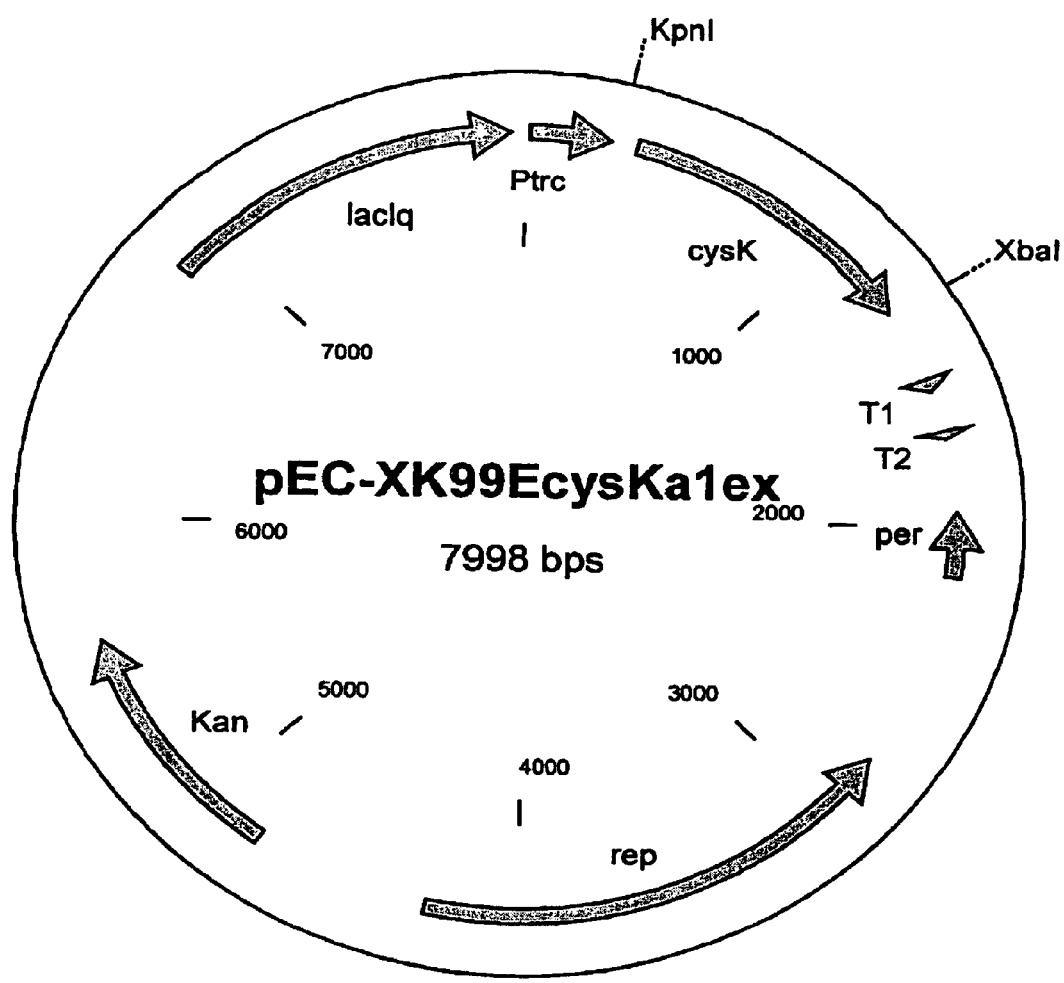

Figure 4: Plasmid pEC-XK99EcysEb1ex
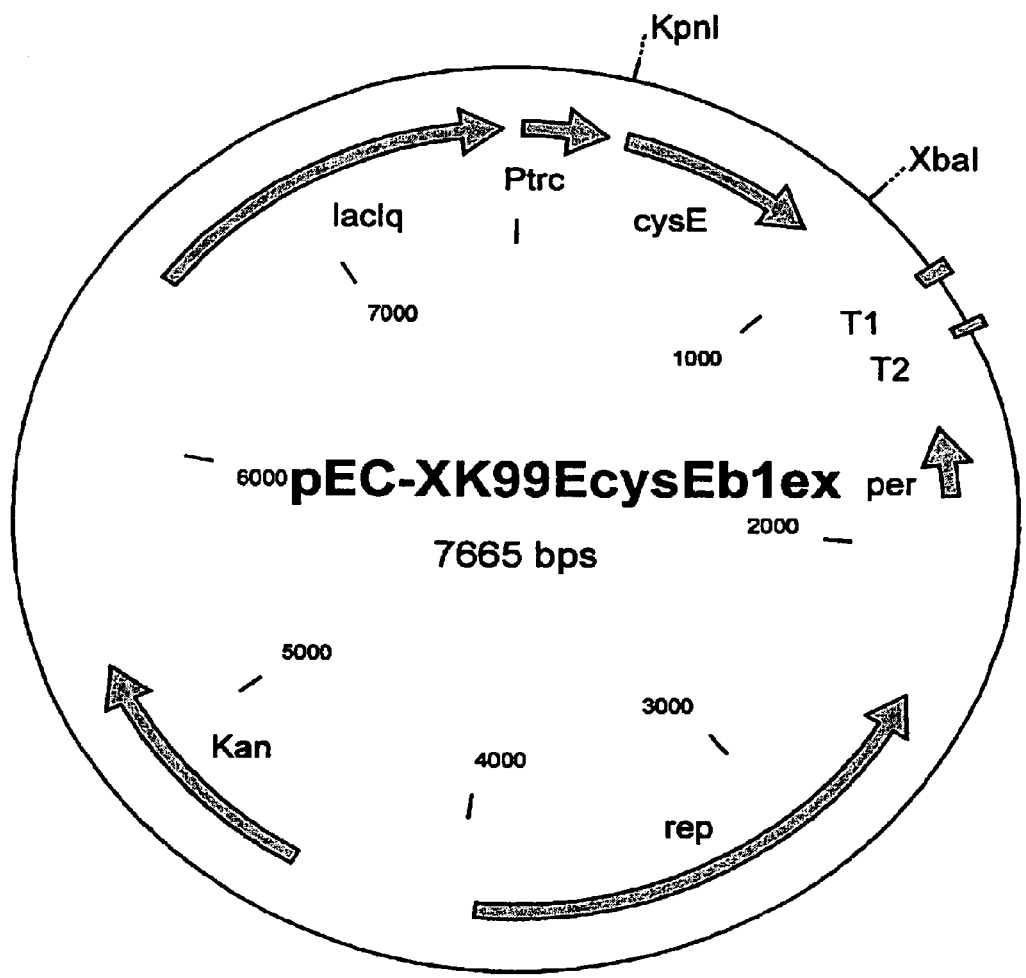

Figure 5: Plasmid pEC-XKcysHa1ex
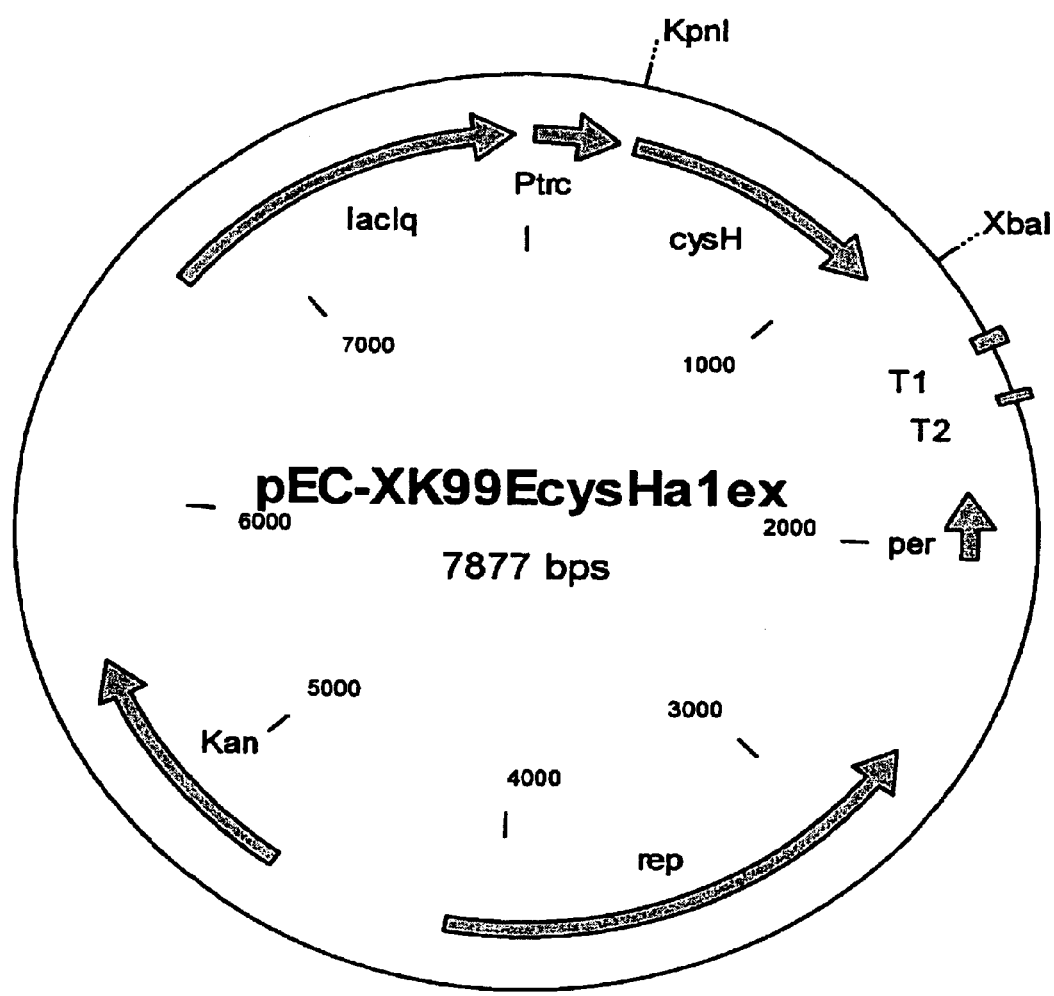

NUCLEOTIDE SEQUENCES WHICH CODE FOR THE CYSD, CYSN, CYSK, CYSE AND CYSH GENES

CROSS-REFERENCE TO RELATED APPLICATIONS

This application claims benefit to U.S. Provisional Application Ser. No. 60/294,223, filed on May 31, 2001 and incorporated herein by reference.

FIELD OF THE INVENTION

The present invention provides nucleotide sequences from coryneform bacteria which code for the cysD, cysN, cysK, cysE and cysH genes and a process for the fermentative preparation of amino acids using bacteria in which the endogene genes mentioned are enhanced.

DESCRIPTION OF THE BACKGROUND

L-Amino acids, in particular L-lysine, L-cysteine and L-methionine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation procedures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

However, there remains a need for improved methods of producing amino acids.

SUMMARY OF THE INVENTION

It is an object of the present invention to provide new methods for improved fermentative preparation of amino acids.

It is another object of the invention to provide nucleic acids which are useful for preparing amino acids.

Accordingly, the present invention provides isolated polynucleotides from coryneform bacteria comprising one or more of the polynucleotide sequences which code for the cysD gene, the cysN gene, the cysK gene, the cysE gene or the cysH gene, selected from the group consisting of (a) polynucleotide which is identical to the extent of at least 70% to a polynucleotide which codes for a polypeptide which comprises the amino acid sequence of SEQ ID No. 2, (b) polynucleotide which is identical to the extent of at least 70% to a polynucleotide which codes for a polypeptide which comprises the amino acid sequence of SEQ ID No. 3, (c) polynucleotide which is identical to the extent of at least 70% to a polynucleotide which codes for a polypeptide which comprises the amino acid sequence of SEQ ID No. 5, (d) polynucleotide which is identical to the extent of at least 70% to a polynucleotide which codes for a polypeptide which comprises the amino acid sequence of SEQ ID No. 6, (e) polynucleotide which is identical to the extent of at least 70% to a polynucleotide which codes for a polypeptide which comprises the amino acid sequence of SEQ ID No. 8, (f) polynucleotide which codes for a polypeptide which comprises an amino acid sequence which is identical to the extent of at least 70% to the amino acid sequence of SEQ ID No. 2, (g) polynucleotide which codes for a polypeptide which comprises an amino acid sequence which is identical to the extent of at least 70% to the amino acid sequence of SEQ ID No. 3, (h) polynucleotide which codes for a polypeptide which comprises an amino acid sequence which is identical to the extent of at least 70% to the amino acid sequence of SEQ ID No. 5, (i) polynucleotide which codes for a polypeptide which comprises an amino acid sequence which is identical to the extent of at least 70% to the amino acid sequence of SEQ ID No. 6, (j) polynucleotide which codes for a polypeptide which comprises an amino acid sequence which is identical to the extent of at least 70% to the amino acid sequence of SEQ ID No. 8, (k) polynucleotide which is complementary to the polynucleotides of (a), (b), (c), (d), (e), (f), (g), (h), (i) or (j), and (l) polynucleotide comprising at least 15 successive nucleotides of the polynucleotide sequence of (a), (b), (c), (d), (e), (f), (g), (h), (i), (j) or (k), where the polypeptides preferably having the corresponding activities, namely of sulfate adenylyl transferase, cysteine synthase A, serine acetyl transferase or 3'-phosphoadenylyl sulfate reductase.

The present invention also provides the above-mentioned polynucleotides, these preferably being DNAs which are capable of replication, comprising:

(i) one or more nucleotide sequences shown in SEQ ID No. 1, SEQ ID No. 4 or SEQ ID No. 7, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The present invention also provides polynucleotides, in particular DNAs, which are capable of replication and comprise one or more nucleotide sequences as shown in SEQ ID No. 1, SEQ ID No.4, or SEQ ID No. 7;

polynucleotides which code for one or more polypeptides which comprises the corresponding amino acid sequences, as shown in SEQ ID No. 2, SEQ ID No.3, SEQ ID No. 5, SEQ ID No. 6, or SEQ ID No. 8;

a vector containing one or more of the polynucleotides according to the invention, in particular shuttle vectors or plasmid vectors, and coryneform bacteria which contain the vector or in which one or more of the endogene genes chosen from the group consisting of the cysD gene, cysN gene, cysK gene, cysE gene and cysH gene is/are enhanced.

The present invention additionally provides a process for the fermentative preparation of amino acids using bacteria in which one or more endogene genes chosen from the group consisting of the cysD gene which codes for the subunit II of sulfate adenylyltransferase, the cysN gene which codes for the subunit I of sulfate adenylyl transferase, the cysK gene which codes for cysteine synthase A, the cysE gene which codes for serine acetyl transferase, the cysH gene which codes for 3'-phosphoadenylyl sulfate reductase is enhanced.

All five endogene genes (cysD gene, cysN gene, cysK gene, cysE gene and cysH gene) participate in the biosynthesis of the sulfur-containing L-amino acids L-cysteine and L-methionine. The carbon matrix of these amino acids is predominantly derived from the same metabolic intermediates as that of the amino acids of the aspartate family, to which L-lysine belongs. Over-expression of one or more of the genes mentioned leads to pool shifts in the participating biosynthesis pathways, which has a positive effect on the formation of L-lysine, L-methionine and L-cysteine.

The present invention also provides a process for the fermentative preparation of an L-amino acid comprising:

(a) fermenting coryneform bacteria in a medium, wherein the bacteria produce the desired L-amino acid and in which at least the cysD gene, cysN gene, cysK gene, cysE gene and/or the cysH gene or nucleotide sequences which code for them is or are enhanced.

(b) concentrating the L-amino acid in the medium or in the cells of the bacteria, and (c) isolating the L-amino acid.

The present invention further provides a process of the preparation of an L-methionine-containing animal feedstuffs additive from a fermentation broth, comprising:

(a) culturing and fermenting an L-methionine-producing microorganism in a fermentation medium;

(b) removing water from the L-methionine-containing fermentation broth;

(c) removing an amount of from 0 to 100 wt. % of the biomass formed during the fermentation; and (d) drying he fermentation broth obtained according to (b) and/or (c) to obtain the animal feedstuffs additive in powder or granule form.

The present invention additionally provides A process of isolating nucleic acids, or polynucleotides or genes, such as RNA, cDNA, or DNA, which code for sulfate adenylyl transferase, cysteine synthase A, serine acetyl transferase and/or 3'-phosphoadenylyl sulfate reductase or have a high similarity with the sequences of the cysD gene, the cysN gene, the cysK gene, the cysE gene and/or the cysH gene, comprising:

contacting a sample with the polynucleotide described above under conditions such that the polynucleotide is capable of hybridizing to another polynucleotide which codes for sulfate adenylyl transferase, cysteine synthase A, serine acetyl transferase and/or 3'-phosphoadenylyl sulfate reductase or have a high similarity with the sequences of the cysD gene, the cysN gene, the cysK gene, the cysE gene and/or the cysH gene.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotides according to the invention according to SEQ ID No. 1, SEQ ID No.4 or SEQ ID No.7 or a fragment thereof, and isolation of the polynucleotide sequence mentioned.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1: Map of the plasmid pEC-XK99E.

FIG. 2: Map of the plasmid pEC-XK99EcysDa1ex.

FIG. 3: Map of the plasmid pEC-XK99EcysKa1ex.

FIG. 4: Map of the plasmid pEC-XK99EcysEb1ex.

FIG. 5: Map of the plasmid pEC-XK99EcysHa1ex.

DETAILED DESCRIPTION OF THE INVENTION

The abbreviations and designations used herein have the following meaning:

Kan: Kanamycin resistance gene aph(3')-IIa from *Escherichia coli*

HindIII: Cleavage site of the restriction enzyme HindIII

XbaI: Cleavage site of the restriction enzyme XbaI

Kpnl: Cleavage site of the restriction enzyme KpnI

Ptrc: trc promoter

T1: Termination region T1

T2: Termination region T2 per: Replication effector per rep: Replication region rep of the plasmid pGA1 lacIq: lacIq repressor of the lac operon of *Escherichia coli* cysD: Cloned cysD gene cysK: Cloned cysK gene cysE: Cloned cysE gene cysH: Cloned cysH gene Where L-amino acids or amino acids are mentioned herein, refers to one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine and the sulfur-containing L-amino acids L-cysteine and L-methionine are particularly preferred.

The terms "L-lysine" or "lysine" refer not only the bases but also the salts, such as e.g. lysine monohydrochloride or lysine sulfate.

The terms "L-cysteine" or "cysteine" refer also to the salts, such as e.g. cysteine hydrochloride or cysteine S-sulfate, of this amino acid.

The terms "L-methionine" or "methionine" also include the salts, such as e.g. methionine hydrochloride or methionine sulfate, of this amino acid.

Polynucleotides which comprise the sequences according to the invention are suitable as hybridization probes for RNA, cDNA and DNA, in order to isolate, in the full length, nucleic acids or polynucleotides or genes which code for sulfate adenylyl transferase, cysteine synthase A, serine acetyl transferase and/or 3'-phosphoadenylyl sulfate reductase, or to isolate those nucleic acids or polynucleotides or genes which have a high similarity of sequence with that of the cysD gene, the cysN gene, the cysK gene, the cysE gene and/or the cysH gene.

Polynucleotides which comprise the sequences according to the invention are furthermore suitable as primers with the aid of which DNA of genes which code for sulfate adenylyl transferase, cysteine synthase A, serine acetyl transferase and/or 3'-phosphoadenylyl sulfate reductase can be prepared by the polymerase chain reaction (PCR).

In one aspect of this invention, the cysD gene according to the invention codes for the subunit II of sulfate adenylyl transferase, the cysN gene according to the invention codes for the subunit I of sulfate adenylyl transferase, the cysK gene according to the invention codes for cysteine synthase A, the cysE gene according to the invention codes for serine acetyl transferase and the cysH gene according to the invention codes for 3'-phosphoadenylyl sulfate reductase.

In another aspect of this invention, it is possible that these genes according to the invention occur in pairs or in combination with several genes, in which case they then code for the combined activities. That is to say, if, for example, the a) cysE gene and cysK gene, or b) cysK gene and cysH gene, or c) cysN gene and cysD gene and cysE gene and cysK gene are enhanced at the same time, these code for a) serine acetyl transferase and cysteine synthase A, b) cysteine synthase A and 3'-phosphoadenylyl sulfate reductase, and c) sulfate adenylyl transferase and serine acetyltransferase and cysteine synthase A.

Such oligonucleotides which serve as probes or primers comprise at least 30, preferably at least 20, very particularly preferably at least 15 successive nucleotides. Oligonucleotides which have a length of at least 40 or 50 nucleotides are also suitable. Oligonucleotides with a length of at least 100, 150, 200, 250 or 300 nucleotides are optionally also suitable.

The term "isolated" refers to a material separated out of its natural environment.

The term "polynucleotide" in general refers to polyribonucleotides and polydeoxyribonucleotides. It being possible for these to be non-modified RNA or DNA or modified RNA or DNA.

The polynucleotides according to the invention include a polynucleotide according to SEQ ID No. 1, SEQ ID No. 4, or SEQ ID No. 7 or a fragment prepared therefrom and also those which are at least 70%, preferably at least 80% and in particular at least 90% to 95% identical to the polynucleotide according to SEQ ID No. 1, SEQ ID No. 4 or SEQ ID No.7 or a fragment prepared therefrom.

The term "polypeptides" refers to peptides or proteins which comprise two or more amino acids bonded via peptide bonds.

The polypeptides according to the invention include the polypeptides according to SEQ ID No. 2, SEQ ID No. 3, SEQ ID No. 5, SEQ ID No. 6 and SEQ ID No. 8, in particular those with the biological activity of sulfate adenylyl transferase, cysteine synthase A, serine acetyl transferase and/or 3'-phosphoadenylyl sulfate reductase, and also those which are at least 70%, preferably at least 80% and in particular at least 90% to 95% identical to the polypeptides according to SEQ ID No. 2, SEQ ID No. 3, SEQ ID No. 5, SEQ ID No. 6 or SEQ ID No. 8 and have the activities mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the cysD gene, the cysN gene, cysE gene, the cysK gene and/or the cysH gene are enhanced, in particular over-expressed.

The term "enhancement" in this respect describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms which the present invention provides can produce L-amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known by those skilled in the art for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The new cysD, cysN, cysK, cysE and cysH genes of *C. glutamicum* which code for the enzymes sulfate adenylyl transferase (EC 2.7.7.4), cysteine synthase A (EC 4.2.99.8), serine acetyl transferase (EC 2.3.1.30) and 3'-phosphoadenylyl sulfate reductase (EC 1.8.99.4) have been isolated.

To isolate the cysD gene, the cysN gene, the cysK gene, the cysE gene, the cysH gene or also other genes of *C. glutamicum*, a gene library of this microorganism is first established in *Escherichia coli* (*E. coli*). The establishment of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was established with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be analyzed with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequences of C. glutamicum which code for the cysD, cysN, cysK, cysE and cysH genes and which, as SEQ ID No. 1, SEQ ID No. 4, and SEQ ID No. 7, are constituents of the present invention have been found. The amino acid sequence of the corresponding proteins has furthermore been derived from the present DNA sequences by the methods described above. The resulting amino acid sequences of the cysD, cysN, cysK, cysE and cysH gene products are shown in SEQ ID No. 2, SEQ ID No. 3, SEQ ID No. 5, SEQ ID No. 6, and SEQ ID No. 8.

Coding DNA sequences which result from SEQ ID No. 1, SEQ ID No. 4 or SEQ ID No. 7 by the degeneracy of the genetic code are also a constituent of the invention. In the same way, DNA sequences which hybridize with SEQ ID No. 1 or parts of SEQ ID No. 1 or SEQ ID No. 4 or parts of SEQ ID No. 4 or SEQ ID No. 7 or parts of SEQ ID No. 7 are a constituent of the invention. Conservative amino acid exchanges, such as e.g. exchange of glycine for alanine or of aspartic acid for glutamic acid in proteins, are furthermore known in the art as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by those skilled in the art, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2, SEQ ID No. 3, SEQ ID No. 5, SEQ ID No. 6 and SEQ ID No. 8 are within the scope of the present invention.

In the same way, DNA sequences which hybridize with SEQ ID No. 1 or parts of SEQ ID No. 1 or SEQ ID No. 4 or parts of SEQ ID No. 4 or SEQ ID No. 7 or parts of SEQ ID No. 7 are a constituent of the invention. Finally, DNA sequences which are prepared by the polymerase chain reaction (PCR) using primers which result from SEQ ID No. 1, SEQ ID No. 4 or SEQ ID No. 7 are a constituent of the invention. Such oligonucleotides typically have a length of at least 15 nucleotides.

Instructions for identifying DNA sequences by means of hybridization, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids in an improved manner after over-expression of one or more of the genes chosen from the group consisting of the cysD gene, cysN gene, cysK gene, cysE gene and cysH gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by those skilled in the art, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in EP 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in WO 96/15246, in Malumbres et al. (Gene 134, 15–24 (1993)), in JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the cysD, cysN, cysK, cysE or cysH genes according to the invention were over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41: 337–342). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the cysD gene, the cysN gene, the cysK gene, the cysE gene and/or the cysH gene.

Thus, for the preparation of L-amino acids, in addition to enhancement of the cysD gene, the cysN gene, the cysK gene, the cysE gene and/or the cysh gene, one or more endogene genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the mqo gene which codes for malate-quinone oxidoreductase (Molenaar et al., European Journal of Biochemistry 254, 395–403 (1998)), the lysC gene which codes for a feed-back resistant aspartate kinase (Accession No.P26512; EP-B-0387527; (EP-A-0699759), the lysE gene which codes for lysine export (DE-A-195 48 222), the hom gene which codes for homoserine dehydrogenase (EP-A 0131171), the ilvA gene which codes for threonine dehydratase (Mockel et al., Journal of Bacteriology (1992) 8065–8072)) or the ilvA(Fbr) allele which codes for a "feed back resistant" threonine dehydratase (Mockel et al., (1994) Molecular Microbiology 13: 833–842), the ilvBN gene which codes for acetohydroxy-acid synthase (EP-B 0356739), the ilvD gene which codes for dihydroxy-acid dehydratase (Sahm and Eggeling (1999) Applied and Environmental Microbiology 65: 1973–1979), the zwa1 gene which codes for the Zwa1 protein (DE: 19959328.0, DSM 13115) can be enhanced, in particular over-expressed.

It may furthermore be advantageous for the production of L-amino acids, in addition to enhancement of the cysD gene, the cysN gene, the cysK gene, the cysE gene and/or the cysH gene, for one or more genes chosen from the group consisting of the pck gene which codes for phosphoenol pyruvate carboxykinase (DE 199 50 409.1; DSM 13047), the pgi gene which codes for glucose 6-phosphate isomerase (U.S. Ser. No. 09/396,478; DSM 12969), the poxB gene which codes for pyruvate oxidase (DE: 1995 1975.7; DSM 13114), the zwa2 gene which codes for the Zwa2 protein (DE: 19959327.2, DSM 13113) to be attenuated, in particular for the expression thereof to be reduced. For the production of L-cysteine in particular, it may be advantageous, in addition to enhancement of the cysD gene, the cysN gene, the cysK gene, the cysE gene and/or the cysh gene, for one or more genes chosen from the group consisting of the aecD gene which codes for cystathionine β-lyase (Accession Number M89931 des National Center for Biotechnology Information (NCBI, Bethesda, Md., USA), the metB gene which codes for cystathione synthase (Accession Number AF1236953 des National Center for Biotechnology Information (NCBI, Bethesda, Md., USA) to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

In addition to over-expression of the cysD gene, the cysN gene, the cysK gene, the cysE gene and/or the cysH gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus.

Organic and inorganic sulfur-containing compounds, such as, for example, sulfides, sulfites, sulfates and thiosulfates, can be used as a source of sulfur, in particular for the preparation of sulfur-containing amino acids.

The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The fermentation broths obtained in this way, in particular containing L-methionine, usually have a dry weight of 7.5 to 25 wt. % and contain L-methionine. It is also advantageous if the fermentation is conducted in a sugar-limited procedure at least at the end, but in particular over at least 30% of the duration of the fermentation. That is to say, the concentration of utilizable sugar in the fermentation medium is reduced to $\geq 0$ to 3 g/l during this period.

The fermentation broth prepared in this manner, in particular containing L-methionine, is then further processed. Depending on requirements, the all or some of the biomass can be removed from the fermentation broth by separation methods, such as e.g. centrifugation, filtration, decanting or a combination thereof, or it can be left completely in this. This broth is then thickened or concentrated by known methods, such as e.g. with the aid of a rotary evaporator, thin film evaporator, falling film evaporator, by reverse osmosis, or by nanofiltration. This concentrated fermentation broth can then be worked up by methods of freeze drying, spray drying, spray granulation or by other processes to give a preferably free-flowing, finely divided powder.

This free-flowing, finely divided powder can then in turn by converted by suitable compacting or granulating processes into a coarse-grained, readily free-flowing, storable and largely dust-free product. In the granulation or compacting it is advantageous to employ conventional organic or inorganic auxiliary substances or carriers, such as starch, gelatin, cellulose derivatives or similar substances, such as are conventionally used as binders, gelling agents or thickeners in foodstuffs or feedstuffs processing, or further substances, such as, for example, silicas, silicates or stearates.

"Free-flowing" is understood as meaning powders which flow unimpeded out of the vessel with the opening of 5 mm (millimeters) of a series of glass outflow vessels with outflow openings of various sizes (Klein, Seifen, Öle, Fette, Wachse 94, 12 (1968)).

As described here, "finely divided" means a powder with a predominant content (>50%) with a particle size of 20 to 200 μm diameter. "Coarse-grained" means products with a predominant content (>50%) with a particle size of 200 to 2000 μm diameter. In this context, "dust-free" means that the product contains only small contents (<5%) with particle sizes of less than 20 μm diameter. The particle size determination can be carried out with methods of laser diffraction spectrometry. The corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, Verlag Wiley & Sons (1998).

"Storable" in the context of this invention means a product which can be stored for up to 120 days, preferably up to 52 weeks, particularly preferably 60 months, without a substantial loss (<5%) of methionine occurring.

Alternatively, however, the product can be absorbed on to an organic or inorganic carrier substance which is known and conventional in feedstuffs processing, such as, for example, silicas, silicates, grits, brans, meals, starches, sugars or others, and/or mixed and stabilized with conventional thickeners or binders. Use examples and processes in this context are described in the literature (Die Mühle+Mischfuttertechnik 132 (1995) 49, page 817).

Finally, the product can be brought into a state in which it is stable to digestion by animal stomachs, in particular the stomach of ruminants, by coating processes ("coating") using film-forming agents, such as, for example, metal carbonates, silicas, silicates, alginates, stearates, starches, gums and cellulose ethers, as described in DE-C-4100920.

If the biomass is separated off during the process, further inorganic solids, for example added during the fermentation, are in general removed. In addition, the animal feedstuffs additive according to the invention comprises at least the predominant proportion of the further substances, in particular organic substances, which are formed or added and are present in solution in the fermentation broth, where these have not been separated off by suitable processes.

In one aspect of the invention, the biomass can be separated off to the extent of up to 70%, preferably up to 80%, preferably up to 90%, preferably up to 95%, and particularly preferably up to 100%. In another aspect of the invention, up to 20% of the biomass, preferably up to 15%, preferably up to 10%, preferably up to 5%, particularly preferably no biomass is separated off.

These organic substances include organic by-products which are optionally produced, in addition to the L-methionine, and optionally discharged by the microorganisms employed in the fermentation. These include L-amino acids chosen from the group consisting of L-lysine, L-valine, L-threonine, L-alanine or L-tryptophan. They include vitamins chosen from the group consisting of vitamin B1 (thiamine), vitamin B2 (riboflavin), vitamin B5 (pantothenic acid), vitamin B6 (pyridoxine), vitamin B12 (cyanocobalamin), nicotinic acid/nicotinamide and vitamin E (tocopherol). They include furthermore organic acids which carry one to three carboxyl groups, such as, for example, acetic acid, lactic acid, citric acid, malic acid or fumaric acid. Finally, they also include sugars, such as, for example, trehalose. These compounds are optionally desired if they improve the nutritional value of the product.

These organic substances, including L-methionine and/or D-methionine and/or the racemic mixture D,L-methionine, can also be added, depending on requirements, as a concentrate or pure substance in solid or liquid form during a suitable process step. These organic substances mentioned can be added individually or as mixtures to the resulting or concentrated fermentation broth, or also during the drying or granulation process. It is likewise possible to add an organic substance or a mixture of several organic substances to the fermentation broth and a further organic substance or a further mixture of several organic substances during a later process step, for example granulation.

The product described above is suitable as a feedstuffs additive, i.e. feed additive, for animal nutrition.

The L-methionine content of the animal feedstuffs additive is conventionally 1 wt. % to 80 wt. %, preferably 2 wt. % to 80 wt. %, particularly preferably 4 wt. % to 80 wt. %, and very particularly preferably 8 wt. % to 80 wt. %, based on the dry weight of the animal feedstuffs additive. Contents of 1 wt. % to 60 wt. %, 2 wt. % to 60 wt. %, 4 wt. % to 60 wt. %, 6 wt. % to 60 wt. %, 1 wt. % to 40 wt. %, 2 wt. % to 40 wt. % or 4 wt. % to 40 wt. % are likewise possible. The water content of the feedstuffs additive is conventionally up to 5 wt. %, preferably up to 4 wt. %, and particularly preferably less than 2 wt. %.

The invention accordingly also provides a process for the preparation of an L-methionine-containing animal feedstuffs additive from fermentation broths, which comprises the steps (a) culture and fermentation of an L-methionine-producing microorganism in a fermentation medium;

(b) removal of water from the L-methionine-containing fermentation broth (concentration);

(c) removal of an amount of 0 to 100 wt. % of the biomass formed during the fermentation; and (d) drying of the fermentation broth obtained according to a) and/or b) to obtain the animal feedstuffs additive in the desired powder or granule form.

If desired, one or more of the following steps can furthermore be carried out in the process according to the invention:

(e) addition of one or more organic substances, including L-methionine and/or D-methionine and/or the racemic mixture D,L-methionine, to the products obtained according to a), b) and/or c);

(f) addition of auxiliary substances chosen from the group consisting of silicas, silicates, stearates, grits and bran to the substances obtained according to a) to d) for stabilization and to increase the storability; or (g) conversion of the substances obtained according to a) to e) into a form which is stable in an animal stomach, in particular rumen, by coating with film-forming agents.

Methods for the determination of L-amino acids are known from the literature. The anlysis can thus be carried out, for example, as described by Spackman et al. (Analytical Chemistry, 30, (1958), 1190) by ion exchange chromatography with subsequent ninhydrin derivation, or it can be carried out by reversed phase HPLC, for example as described by Lindroth et al. (Analytical Chemistry (1979) 51: 1167–1174).

The process according to the invention is used for fermentative preparation of amino acids.

The following microorganisms were deposited as a pure culture on May 18, 2001 at the Deutsche Sammlung für Mikroorganismen und Zellkulturen (DSMZ=German Collection of Microorganisms and Cell Cultures, Braunschweig, Germany) in accordance with the Budapest Treaty:

*E. coli* DH5αmcr/pEC-XK99EcysEb1ex as DSM 14308,
*E. coli* DH5αmcr/pEC-XK99EcysKa1ex as DSM 14310,
*E. coli* DH5 αmcr/pEC-XK99EcysDa1ex as DSM 14311,
*E. coli* DH5αmcr/pEC-XK99EcysHa1ex as DSM 14315.

EXAMPLES

Having generally described this invention, a further understanding can be obtained by reference to certain specific examples which are provided herein for purposes of illustration only and are not intended to be limiting unless otherwise specified.

The isolation of plasmid DNA from Escherichia coli and all techniques of restriction, Klenow and alkaline phosphatase treatment were carried out by the method of Sambrook et al. (Molecular Cloning. A Laboratory Manual (1989) Cold Spring Harbour Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

Example 1

Preparation of a Genomic Cosmid Gene Library

From *Corynebacterium Glutamicum* ATCC 13032

Chromosomal DNA from *Corynebacterium glutamicum* ATCC 13032 was isolated as described by Tauch et al.

(1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164), obtained from Stratagene (La Jolla, USA, Product Description SuperCos 1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM MgSO$_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

Example 2

Isolation and Sequencing of the cysD Gene, the cysN Gene, the cysK Gene, the cysE Gene or the cysH Gene The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97–0. The individual sequences of the pZero 1 derivatives were assembled to a continuous contig. The computer-assisted coding region analysis was prepared with the XNIP program (Staden, 1986, Nucleic Acids Research, 14:217–231).

The resulting nucleotide sequences are shown in SEQ ID No. 1 SEQ ID No. 4 and SEQ ID No. 7. Analysis of the nucleotide sequences showed six open reading frames of 915 base pairs, 1302 base pairs, 936 base pairs, 567 base pairs and 786 base pairs, which were called the cysD gene, cysN gene, cysK gene, cysE gene and cysH gene. The cysD gene codes for a protein of 304 amino acids, the cysN gene codes for a protein of 433 amino acids, the cysK gene codes for a protein of 311 amino acids, the cysE gene codes for a protein of 188 amino acids and the cysH gene codes for a protein of 261 amino acids.

Example 3

Preparation of Shuttle Expression Vectors Based on pEC-XK99E for Enhancement of the cysD, cysK, cysE and cysH Genes in *C. Glutamicum*

3.1 Amplification of the cysD, cysK, cysE and cysh Genes

From the strain ATCC 13032, chromosomal DNA was isolated by the method of Eikmanns et al. (Microbiology 140: 1817–1828 (1994)). On the basis of the sequences of the cysD, cysK, cysE and cysH genes known for *C. glutamicum* from Example 2, the following oligonucleotides, listed in Table 1, were chosen for the polymerase chain reaction (see SEQ ID No. 9, SEQ ID No. 10, SEQ ID No. 11, SEQ ID No. 12, SEQ ID No. 13, SEQ ID No. 14, SEQ ID No. 15 and SEQ ID No. 16). In addition, suitable restriction cleavage sites which allow cloning into the target vector were inserted into the primers. They are listed in Table 1 and identified by underlining in the nucleotide sequence.

TABLE 1

| Primer | Sequence with restriction cleavage site | Amplified fragment |
|---|---|---|
| cysDex1 | 5'-ct<u>ggtacc</u>-gcggacttcactcatgacca-3'<br>KpnI | cysD<br>(1017 bp) |

TABLE 1-continued

| Primer | Sequence with restriction cleavage site | Amplified fragment |
|---|---|---|
| cysDex2 | 5'-cgtctaga-ggaacctgcggtgcacagac-3' XbaI | |
| cysKex1 | 5'-agggtacc-caagcggtcgaccaacaaaa-3' KpnI | cysK (1005 bp) |
| cysKex2 | 5'-cttctaga-attagtcgcggatgtcttcg-3' XbaI | |
| cysEex1 | 5'-ctggtacc-tcacgctgttagacttgcct-3' KpnI | cysE (672 bp) |
| cysEex2 | 5'-gatctaga-acaaacgcactctggagctt-3' XbaI | |
| cysHex1 | 5'-acggtacc-tgagtcgcaacaatgagctt-3' KpnI | cysH (884 bp) |
| cysHex2 | 5'-gttctaga-cggaggatgtggatggattc-3' XbaI | |

The primers shown were synthesized by MWG-Biotech AG (Ebersberg, Germany) and the PCR reaction was carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment 1017 bp in size, which carries the cysD gene, and a DNA fragment 1005 bp in size, which carries the cysK gene, a DNA fragment 672 bp in size, which carries the cysE gene, and a DNA fragment 884 bp in size, which carries the cysH gene.

The cysD fragment, the cysK fragment, the cysE fragment and the cysh fragment were cleaved with the restriction endonucleases KpnI and XbaI and then isolated from the agarose gel with the QiaExII Gel Extraction Kit (Product No. 20021, Qiagen, Hilden, Germany).

3.2 Construction of the Shuttle Vector pEC-XK99E

The *E. coli—C. glutamicum* shuttle vector pEC-XK99E was constructed according to techniques well-known to those skilled in the art. The vector contains the replication region rep of the plasmid pGA 1 including the replication effector per (U.S. Pat. No. 5,175,108; Nesvera et al., Journal of Bacteriology 179, 1525–1532 (1997)), the kanamycin resistance gene aph(3')-IIa from *Escherichia coli* (Beck et al. (1982), Gene 19: 327–336), the replication origin of the trc promoter, the termination regions T1 and T2, the lacI$^q$ gene (repressor of the lac operon of *E. coli*) and a multiple cloning site (mcs) (Norrander, J. M. et al. Gene 26, 101–106 (1983)) of the plasmid pTRC99A (Amann et al. (1988), Gene 69: 301–315).

The *E. coli—C. glutamicum* shuttle vector pEC-XK99E constructed was transferred into *C. glutamicum* DSM5715 by means of electroporation (Liebl et al., 1989, FEMS Microbiology Letters, 53:299–303). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonuclease HindIII, and the plasmid was checked by subsequent agarose gel electrophoresis.

The plasmid construct thus obtained in this way was called pEC-XK99E and is shown in FIG. 1. The strain obtained by electroporation of the plasmid pEC-XK99E in the C. glutamicum strain DSM5715 was called DSM5715/pEC-XK99E and deposited as DSM 13455 at the Deutsche Sammlung für Mikroorganismen und Zellkulturen (DSMZ= German Collection of Microorganisms and Cell Cultures, Braunschweig, Germany) in accordance with the Budapest Treaty.

3.3 Cloning of the cysD, cysK, cysE and cysH Genes in the *E. coli—C. Glutamicum* Shuttle Vector pEC-XK99E The *E. coli—C. glutamicum* shuttle vector pEC-XK99E described in Example 3.1 was used as the vector. DNA of this plasmid was cleaved completely with the restriction enzymes KpnI and XbaI and then dephosphorylated with shrimp alkaline phosphatase (Roche Diagnostics GmbH, Mannheim, Germany, Product Description SAP, Product No. 1758250).

The fragments cysD, approx. 1000 bp in size, cysK, approx. 990 bp in size, cysE, approx. 660 bp in size and cysH, approx. 870 bp in size cleaved with the restriction enzymes KpnI and XbaI and isolated from the agarose gel were in each case mixed with the prepared vector pEC-XK99E and the batches were treated with T4 DNA ligase (Amersham Pharmacia, Freiburg, Germany, Product Description T4-DNA-Ligase, Code no. 27-0870-04).

The ligation batches were transformed in the *E. coli* strain DH5αmcr (Hanahan, In: DNA Cloning. A Practical Approach. Vol. I, IRL-Press, Oxford, Washington D.C., USA). Selection of plasmid-carrying cells was made by plating out the transformation batches on LB agar (Lennox, 1955, Virology, 1:190) with 50 mg/l kanamycin. After incubation overnight at 37° C., recombinant individual clones were selected. Plasmid DNA was isolated from a transformant in each case with the Qiaprep Spin Miniprep Kit (Product No. 27106, Qiagen, Hilden, Germany) in accordance with the manufacturer's instructions and cleaved with the restriction enzymes KpnI and XbaI to check the plasmid by subsequent agarose gel electrophoresis. The plasmids obtained were called pEC-XK99EcysDalex, pEC-XK99EcysKalex, pEC-XK99EcysEb1ex and pEC-XK99EcysHalex. They are shown in FIGS. 2, 3, 4 and 5.

Example 4

Transformation of the Strain DSM5715 with the Plasmids pEC-XK99EcysDa1ex, pEC-XK99EcysKa1ex, pEC-XK99EcysEb1ex and pEC-XK99EcysHa1ex The strain DSM5715 was transformed with in each case one of the plasmids pEC-XK99EcysDa1ex, pEC-XK99EcysKa1ex, pEC-XK99EcysEb1ex and pEC-XK99EcysHa1ex using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant in each case by conventional methods (Peters-Wendisch et al., 1998, Microbiology 144, 915–927). DNA of the plasmids pEC-XK99EcysDa1ex, pEC-XK99EcysKa1ex, pEC-XK99EcysEb1ex and pEC-XK99EcysHa1ex were cleaved with the restriction endonucleases KpnI and XbaI. The plasmids were checked by subsequent agarose gel electrophoresis. The strains obtained were called DSM5715pEC-XK99EcysDa1ex, DSM5715/pEC-XK99EcysKa1ex, DSM5715/pEC-XK99EcysEb1ex or DSM5715/pEC-XK99EcysHa1ex.

Example 5

Preparation of Lysine

The *C. glutamicum* strains DSM5715/pEC-XK99EcysDa1ex, DSM5715/pEC-XK99EcysKa1ex, DSM5715/pEC-XK99EcysEb1ex or DSM5715/pEC-XK99EcysHa1ex obtained in Example 4 were cultured in a nutrient medium suitable for the production of lysine and the lysine content in the culture supernatant of each strain was determined.

For this, the strains were first incubated on an agar plate with the corresponding antibiotic (brain-heart agar with kanamycin (25 mg/l)) for 24 hours at 33° C. Starting from this agar plate culture, in each case a preculture was seeded (10 ml medium in a 100 ml conical flask). The complete medium CgIII was used as the medium for the precultures.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The precultures were incubated for 16 hours at 33° C. at 240 rpm on a shaking machine. In each case a main culture was seeded from these precultures such that the initial OD (660 nm) of the main cultures was 0.1. Medium MM was used for the main cultures.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in-the dry state.

Culturing was carried out in a 10 ml volume in a 100 ml conical flask with baffles. Kanamycin (25 mg/l) was added. Culturing was carried out at 33° C. and 80% atmospheric humidity After 48 hours the OD of the cultures DSM5715, DSM5715/pEC-XK99EcysDa1ex, DSM5715/pEC-XK99EcysKa1ex and DSM5715/pEC-XK99EcysHa1ex and after 72 hours the OD of the culture DSM5715/pEC-XK99EcysEb1ex was determined at a measurement wavelength of 660 nm with a Biomek 1000 (Beckmann Instruments GmbH, Munich). The amount of lysine formed was in each case determined with an amino acid analyzer from Eppendorf-BioTronik (Hamburg, Germany) by ion exchange chromatography and post-column derivation with ninhydrin detection.

The result of the experiment is shown in Tables 2 and 3.

TABLE 2

| Strain | OD (660 nm) (48 h) | Lysine HCl g/l (48 h) |
|---|---|---|
| DSM5715 | 11.3 | 13.11 |
| DSM5715/pEC-XK99EcysDa1ex | 13.7 | 13.54 |
| DSM5715/pEC-XK99EcysKa1ex | 13.5 | 14.35 |
| DSM5715/pEC-XK99EcysHa1ex | 11.5 | 15.22 |

TABLE 3

| Strain | OD (660 nm) (72 h) | Lysine HCl (72 h) g/l |
|---|---|---|
| DSM5715 | 7.17 | 14.27 |
| DSM5715/pEC-XK99EcysEb1ex | 9.0 | 15.22 |

Obviously, numerous modifications and variations of the present invention are possible in light of the above teachings. It is therefore to be understood that within the scope of the appended claims, the invention may be practiced otherwise than as specifically described herein.

The publications cited above are incorporated herein by reference.

This application is based on German Patent Application Serial Nos. 100 48 603.7, filed on Sep. 30, 2000, 101 09 691.7, filed on Feb. 28, 2001, and 101 36 986.7, filed on Jul. 28, 2001, each of which is incorporated herein by reference.

What is claimed is:

1. An isolated polynucleotide selected from the group consisting of (a) a polynucleotide which is cysD and which codes for a polypeptide which comprises the amino acid sequence of SEQ ID No. 2, (b) a polynucleotide which is cysN and which codes for a polypeptide which comprises the amino acid sequence of SEQ ID No. 3, (c) a polynucleotide which is cysK and which codes for a polypeptide which comprises the amino acid sequence of SEQ ID No. 5, (d) a polynucleotide which is cysE and which codes for a polypeptide which comprises the amino acid sequence of SEQ ID No. 6, and (e) a polynucleotide which is cysH and which codes for a polypeptide which comprises the amino acid sequence of SEQ ID No. 8.

2. The isolated polynucleotide of claim 1, wherein the polypeptide comprising the amino acid sequence of SEQ ID NO:2 has sulfate adenylyltransferase activity, the polypeptide comprising the amino acid sequence of SEQ ID NO:3 has adenylyltransferase activity, the polypeptide comprising the amino acid sequence of SEQ ID NO:5 has cysteine synthase A activity, the polypeptide comprising the amino acid sequence of SEQ ID NO:6 has serine acetyltransferase activity, and the polypeptide comprising the amino acid sequence of SEQ ID NO:8 has 3'-phopshoadenylyl sulfate reductase.

3. The isolated polynucleotide of claim 1, wherein the polynucleotide is DNA.

4. The isolated polynucleotide of claim 1, wherein the polynucleotide is an RNA.

5. An isolated polynucleotide, comprising a nucleic acid sequence selected from the group consisting of nucleotides 232 to 1143 of SEQ ID No. 1, nucleotides 1146 to 2444 of SEQ ID No. 1, nucleotides 271 to 1203 of SEQ ID No. 4, nucleotides 1392 to 1955 of SEQ ID No.4, and nucleotides 250 to 1032 of SEQ ID No. 7.

6. The isolated polynucleotide of claim 3, comprising:

(i) the nucleotide sequence shown in SEQ ID No. 1, SEQ ID No.4 or SEQ ID No. 7, (ii) at least one degenerate sequence which corresponds to sequence (i), or (iii) at least one sequence which hybridizes with the sequence fully complementary to sequence (i) or (ii) wherein the hybridization conditions comprise washing in 2 × SSC at a temperature of from 50 to 68° C. and which encodes a polypeptide with an activity selected from the group consisting of sulfate adenylyltransferase activity, adenylyltransferase activity, cysteine synthase A activity, serine acetyltransferase activity, and 3'-phopshoadenylyl sulfate reductase activity.

7. The isolated polynucleotide of claim 1, which is (a).
8. The isolated polynucleotide of claim 1, which is (b).
9. The isolated polynucleotide of claim 1, which is (c).
10. The isolated polynucleotide of claim 1, which is (d).
11. The isolated polynucleotide of claim 1, which is (e).
12. An isolated polynucleotide comprising the full complement of SEQ ID NO:1, SEQ ID NO:4, or SEQ ID NO:7.
13. A vector comprising the isolated polynucleotide of claim 1.
14. A vector comprising the isolated polynucleotide of claim 5.
15. A vector comprising the isolated polynucleotide of claim 6.
16. A vector comprising the isolated polynucleotide of claim 7.
17. A vector comprising the isolated polynucleotide of claim 8.
18. A vector comprising the isolated polynucleotide of claim 9.
19. A vector comprising the isolated polynucleotide of claim 10.
20. A vector comprising the isolated polynucleotide of claim 11.
21. A vector comprising the isolated polynucleotide of claim 12.

* * * * *

SEQUENCE LISTING

```
<160> NUMBER OF SEQ ID NOS: 16

<210> SEQ ID NO 1
<211> LENGTH: 2640
<212> TYPE: DNA
<213> ORGANISM: Corynebacterium glutamicum
<220> FEATURE:
<221> NAME/KEY: CDS
<222> LOCATION: (232)..(1143)
<223> OTHER INFORMATION:
<221> NAME/KEY: CDS
<222> LOCATION: (1146)..(2444)
<223> OTHER INFORMATION:
```

```
<400> SEQUENCE: 1
tgcgctgagc ttggatgcca ccggcaggct caagatttct ccaattatca cctggtcatt      60
ggaggaaacc aacgagttca ttgcggacaa caacctcatc gatcacccac ttacccatca     120
gggttatcca tcaattggat gcgaaacctg caccttcct gttgctgaag gacaagaccc      180
tagggccggc cgttgggctg aaacgccaa gacagaatgc ggacttcact c atg acc      237
                                                       Met Thr
                                                         1
```

| | | | | | | | | | | | | | | | | |
|---|---|---|---|---|---|---|---|---|---|---|---|---|---|---|---|---|
| aca | acc | gtt | gca | tca | gta | cta | tcc | cca | cac | ctt | aaa | gat | ctt | gaa | aat | 285 |
| Thr | Thr | Val | Ala | Ser | Val | Leu | Ser | Pro | His | Leu | Lys | Asp | Leu | Glu | Asn | |
| | | 5 | | | | | 10 | | | | | 15 | | | | |
| gaa | tcc | atc | cac | atc | ctc | cgc | gag | gta | gct | ggc | cag | ttt | gat | aag | gtc | 333 |
| Glu | Ser | Ile | His | Ile | Leu | Arg | Glu | Val | Ala | Gly | Gln | Phe | Asp | Lys | Val | |
| | 20 | | | | | 25 | | | | | 30 | | | | | |
| ggc | ctg | ctg | ttt | tcc | ggc | ggt | aag | gat | tcc | gtc | gtg | gtg | tac | gag | ctt | 381 |
| Gly | Leu | Leu | Phe | Ser | Gly | Gly | Lys | Asp | Ser | Val | Val | Val | Tyr | Glu | Leu | |
| 35 | | | | | 40 | | | | | 45 | | | | | 50 | |
| gcg | cgc | cgc | gct | ttc | gct | cca | gct | aac | gtg | cct | ttt | gaa | ttg | ctg | cac | 429 |
| Ala | Arg | Arg | Ala | Phe | Ala | Pro | Ala | Asn | Val | Pro | Phe | Glu | Leu | Leu | His | |
| | | | | 55 | | | | | 60 | | | | | 65 | | |
| gtg | gac | acc | ggc | cac | aac | ttc | cca | gag | gtt | ttg | gaa | ttc | cgc | gac | aac | 477 |
| Val | Asp | Thr | Gly | His | Asn | Phe | Pro | Glu | Val | Leu | Glu | Phe | Arg | Asp | Asn | |
| | | 70 | | | | | 75 | | | | | 80 | | | | |
| ctg | gtg | gag | cgc | acc | ggc | gcc | cgc | ctg | cgc | gta | gct | aaa | gtc | cag | gac | 525 |
| Leu | Val | Glu | Arg | Thr | Gly | Ala | Arg | Leu | Arg | Val | Ala | Lys | Val | Gln | Asp | |
| | 85 | | | | | 90 | | | | | 95 | | | | | |
| tgg | atc | gat | cgc | ggt | gac | ctg | cag | gaa | cgc | cca | gac | ggc | acc | cgc | aac | 573 |
| Trp | Ile | Asp | Arg | Gly | Asp | Leu | Gln | Glu | Arg | Pro | Asp | Gly | Thr | Arg | Asn | |
| 100 | | | | | 105 | | | | | 110 | | | | | | |
| cca | ctg | cag | act | gtc | cct | ttg | gtg | gag | acc | atc | gct | gag | cag | ggc | tac | 621 |
| Pro | Leu | Gln | Thr | Val | Pro | Leu | Val | Glu | Thr | Ile | Ala | Glu | Gln | Gly | Tyr | |
| 115 | | | | | 120 | | | | | 125 | | | | | 130 | |
| gac | gca | gtg | ctt | ggt | ggc | gct | cgc | cgc | gat | gag | gag | cgt | gcc | cgc | gcc | 669 |
| Asp | Ala | Val | Leu | Gly | Gly | Ala | Arg | Arg | Asp | Glu | Glu | Arg | Ala | Arg | Ala | |
| | | | 135 | | | | | 140 | | | | | 145 | | | |
| aag | gag | cgt | gtg | ttc | tct | gtg | cgt | gac | tcc | ttc | ggt | ggt | tgg | gat | cca | 717 |
| Lys | Glu | Arg | Val | Phe | Ser | Val | Arg | Asp | Ser | Phe | Gly | Gly | Trp | Asp | Pro | |
| | | 150 | | | | | 155 | | | | | 160 | | | | |
| cgc | cgt | cag | cgc | cca | gag | ctg | tgg | acc | ctc | tac | aac | ggt | ggc | cac | ctg | 765 |
| Arg | Arg | Gln | Arg | Pro | Glu | Leu | Trp | Thr | Leu | Tyr | Asn | Gly | Gly | His | Leu | |
| | 165 | | | | | 170 | | | | | 175 | | | | | |
| cca | ggc | gaa | aac | atc | cgt | gtt | ttc | cca | atc | tcc | aac | tgg | act | gaa | gct | 813 |
| Pro | Gly | Glu | Asn | Ile | Arg | Val | Phe | Pro | Ile | Ser | Asn | Trp | Thr | Glu | Ala | |
| 180 | | | | | 185 | | | | | 190 | | | | | | |
| gac | att | tgg | gag | tac | atc | ggc | gcc | cgt | ggc | atc | gaa | ctt | cca | ccg | atc | 861 |
| Asp | Ile | Trp | Glu | Tyr | Ile | Gly | Ala | Arg | Gly | Ile | Glu | Leu | Pro | Pro | Ile | |
| 195 | | | | | 200 | | | | | 205 | | | | | 210 | |
| tac | ttc | tcc | cac | gac | cgc | gaa | gtt | ttc | gag | cgc | gac | ggc | atg | tgg | ctg | 909 |
| Tyr | Phe | Ser | His | Asp | Arg | Glu | Val | Phe | Glu | Arg | Asp | Gly | Met | Trp | Leu | |
| | | | | 215 | | | | | 220 | | | | | 225 | | |
| acc | gca | ggc | gag | tgg | ggt | gga | cca | aag | aag | ggc | gag | gag | atc | gtc | acc | 957 |
| Thr | Ala | Gly | Glu | Trp | Gly | Gly | Pro | Lys | Lys | Gly | Glu | Glu | Ile | Val | Thr | |
| | | | 230 | | | | | 235 | | | | | 240 | | | |
| aag | act | gtc | cgc | tac | cgc | acc | gtc | ggc | gat | atg | tcc | tgc | acc | ggt | gct | 1005 |
| Lys | Thr | Val | Arg | Tyr | Arg | Thr | Val | Gly | Asp | Met | Ser | Cys | Thr | Gly | Ala | |
| | | 245 | | | | | 250 | | | | | 255 | | | | |
| gtg | ctc | tcc | gaa | gcc | cgc | acc | att | gac | gat | gtg | atc | gaa | gag | atc | gcc | 1053 |
| Val | Leu | Ser | Glu | Ala | Arg | Thr | Ile | Asp | Asp | Val | Ile | Glu | Glu | Ile | Ala | |
| | 260 | | | | | 265 | | | | | 270 | | | | | |

```
acc tcc acc ctt acc gaa cgt ggc gca acc cgc gcc gat gac cgc ctc       1101
Thr Ser Thr Leu Thr Glu Arg Gly Ala Thr Arg Ala Asp Asp Arg Leu
275                 280                 285                 290 agc gaa tcc gca atg gaa gac cgc aag aag gaa ggc tac ttc tg  atg       1148
Ser Glu Ser Ala Met Glu Asp Arg Lys Lys Glu Gly Tyr Phe     Met
                        295                 300                 305 act gct cca acc ttg aat aaa gca tcc gaa aag att gca tca cgc gag       1196
Thr Ala Pro Thr Leu Asn Lys Ala Ser Glu Lys Ile Ala Ser Arg Glu
                    310                 315                 320 acc ctt cgt ctg tgc acc gca ggt tcc gta gat gat ggc aag tcc acc       1244
Thr Leu Arg Leu Cys Thr Ala Gly Ser Val Asp Asp Gly Lys Ser Thr
                325                 330                 335 ttc gtc ggc cgc ctc ctg cac gac acc aag tct gtt ctt gct gat cag       1292
Phe Val Gly Arg Leu Leu His Asp Thr Lys Ser Val Leu Ala Asp Gln
            340                 345                 350 ctg gct tcc gta gag cgc acc tcc gcc gac cgt ggc ttc gaa ggc ctc       1340
Leu Ala Ser Val Glu Arg Thr Ser Ala Asp Arg Gly Phe Glu Gly Leu
            355                 360                 365 gac ctg tca ctc ctc gtc gac ggc ctg cgc gcc gag cgt gag cag ggc       1388
Asp Leu Ser Leu Leu Val Asp Gly Leu Arg Ala Glu Arg Glu Gln Gly
370                 375                 380                 385 atc acc atc gac gtt gcc tac cgc tac ttc gcc acc gac aag cgc acc       1436
Ile Thr Ile Asp Val Ala Tyr Arg Tyr Phe Ala Thr Asp Lys Arg Thr
                390                 395                 400 ttc atc ctg gct gat acc cca ggt cac gtg cag tac acc cgc aac acc       1484
Phe Ile Leu Ala Asp Thr Pro Gly His Val Gln Tyr Thr Arg Asn Thr
                405                 410                 415 gtc acc ggc gtc tcc acc tcc cag gtt gta gtt ttg ctt gtc gac gcc       1532
Val Thr Gly Val Ser Thr Ser Gln Val Val Val Leu Leu Val Asp Ala
            420                 425                 430 cgc cac ggc gtc gtc gag cag acc cgc cgc cac ctg tcc gta tcg gct       1580
Arg His Gly Val Val Glu Gln Thr Arg Arg His Leu Ser Val Ser Ala
435                 440                 445 ctg ctg ggc gta cgc acg gtg atc ctc gca gtc aac aaa att gac ctt       1628
Leu Leu Gly Val Arg Thr Val Ile Leu Ala Val Asn Lys Ile Asp Leu
450                 455                 460                 465 gtt gat tac agc gaa gaa gtc ttc cgc aac att gaa aag gaa ttc gtt       1676
Val Asp Tyr Ser Glu Glu Val Phe Arg Asn Ile Glu Lys Glu Phe Val
                470                 475                 480 ggc ctg gca tct gca ctt gat gtc aca gac acc cac gtt gtt cca atc       1724
Gly Leu Ala Ser Ala Leu Asp Val Thr Asp Thr His Val Val Pro Ile
                485                 490                 495 tct gcg ctc aag ggc gac aac gtt gca gaa cct tcc acc cac atg gat       1772
Ser Ala Leu Lys Gly Asp Asn Val Ala Glu Pro Ser Thr His Met Asp
            500                 505                 510 tgg tac acc gga cca acc gtg ctg gaa atc ctg gaa aac gta gaa gtt       1820
Trp Tyr Thr Gly Pro Thr Val Leu Glu Ile Leu Glu Asn Val Glu Val
515                 520                 525 tcc cac ggc cgt gca cac gac ctg ggc ttc cgc ttc cca atc cag tac       1868
Ser His Gly Arg Ala His Asp Leu Gly Phe Arg Phe Pro Ile Gln Tyr
530                 535                 540                 545 gtc atc cgc gag cac gcc acc gac tac cgt ggc tac gcc ggc acc atc       1916
Val Ile Arg Glu His Ala Thr Asp Tyr Arg Gly Tyr Ala Gly Thr Ile
                550                 555                 560 aac gct ggt tcc gtc tcc gtg ggc gat acc gtg tac cta cct gaa ggc       1964
Asn Ala Gly Ser Val Ser Val Gly Asp Thr Val Tyr Leu Pro Glu Gly
            565                 570                 575 cgc acc acc cag gtc acc cac atc gat tcc gct gac gga tcc ctc cag       2012
Arg Thr Thr Gln Val Thr His Ile Asp Ser Ala Asp Gly Ser Leu Gln
```

-continued

```
          580              585              590
acc gca tca gtt gga gaa gcc gtt gtc ctg cgc cta gcc cag gaa atc    2060
Thr Ala Ser Val Gly Glu Ala Val Val Leu Arg Leu Ala Gln Glu Ile
    595              600              605 gac ctc atc cgc ggc gaa ctc atc gct ggc gaa gac cgc cca gaa tcc    2108
Asp Leu Ile Arg Gly Glu Leu Ile Ala Gly Glu Asp Arg Pro Glu Ser
610              615              620              625 gtt cgc tcc ttc aac gcc act gtt gtt ggc ttg gcc gat cgc acc atc    2156
Val Arg Ser Phe Asn Ala Thr Val Val Gly Leu Ala Asp Arg Thr Ile
                630              635              640 aaa cca ggt gca gca gtc aag gtt cgc tac ggc acc gag ctg gtc cgc    2204
Lys Pro Gly Ala Ala Val Lys Val Arg Tyr Gly Thr Glu Leu Val Arg
            645              650              655 gga cgc gtc gca gcc atc gaa cga gtc ctc gac atc gac ggc gtc aac    2252
Gly Arg Val Ala Ala Ile Glu Arg Val Leu Asp Ile Asp Gly Val Asn
        660              665              670 gac aac gaa gca cca gaa acc tac ggc ctc aac gac atc gca cac gtg    2300
Asp Asn Glu Ala Pro Glu Thr Tyr Gly Leu Asn Asp Ile Ala His Val
    675              680              685 cgc atc gac gtt gca ggc gaa ctc gaa gtt gaa gat tac gct gcc cgc    2348
Arg Ile Asp Val Ala Gly Glu Leu Glu Val Glu Asp Tyr Ala Ala Arg
690              695              700              705 ggc gcc atc gga tcc ttc ctc ctc atc gac caa tcc tcc ggc gat acc    2396
Gly Ala Ile Gly Ser Phe Leu Leu Ile Asp Gln Ser Ser Gly Asp Thr
                710              715              720 ctc gca gct ggc ttg gtt ggc cac cgc cta cgc aat aac tgg tcg atc    2444
Leu Ala Ala Gly Leu Val Gly His Arg Leu Arg Asn Asn Trp Ser Ile
            725              730              735 tagaccagtg tcttaggcaa gaccccattt aggacacctc atgattcccc tgattacgct    2504
ttcccacggt tcccgcaaaa agtccgcagc tgcaggcatt actgcgctga ctcatgaggc    2564
cggacgaatg ctggaaacac cagccgtgga agcgcattta gagcttgctg aaccttccct    2624
tgatcaggtt gtggca                                                      2640

<210> SEQ ID NO 2
<211> LENGTH: 304
<212> TYPE: PRT
<213> ORGANISM: Corynebacterium glutamicum

<400> SEQUENCE: 2

Met Thr Thr Thr Val Ala Ser Val Leu Ser Pro His Leu Lys Asp Leu
1               5                   10                  15

Glu Asn Glu Ser Ile His Ile Leu Arg Glu Val Ala Gly Gln Phe Asp
            20                  25                  30

Lys Val Gly Leu Leu Phe Ser Gly Gly Lys Asp Ser Val Val Val Tyr
        35                  40                  45

Glu Leu Ala Arg Arg Ala Phe Ala Pro Ala Asn Val Pro Phe Glu Leu
    50                  55                  60

Leu His Val Asp Thr Gly His Asn Phe Pro Glu Val Leu Glu Phe Arg
65                  70                  75                  80

Asp Asn Leu Val Glu Arg Thr Gly Ala Arg Leu Arg Val Ala Lys Val
                85                  90                  95

Gln Asp Trp Ile Asp Arg Gly Asp Leu Gln Glu Arg Pro Asp Gly Thr
            100                 105                 110

Arg Asn Pro Leu Gln Thr Val Pro Leu Val Glu Thr Ile Ala Glu Gln
        115                 120                 125

Gly Tyr Asp Ala Val Leu Gly Gly Ala Arg Arg Asp Glu Glu Arg Ala
```

```
                130                 135                 140
Arg Ala Lys Glu Arg Val Phe Ser Val Arg Asp Ser Phe Gly Gly Trp
145                 150                 155                 160

Asp Pro Arg Arg Gln Arg Pro Glu Leu Trp Thr Leu Tyr Asn Gly Gly
                165                 170                 175

His Leu Pro Gly Glu Asn Ile Arg Val Phe Pro Ile Ser Asn Trp Thr
            180                 185                 190

Glu Ala Asp Ile Trp Glu Tyr Ile Gly Ala Arg Gly Ile Glu Leu Pro
        195                 200                 205

Pro Ile Tyr Phe Ser His Asp Arg Glu Val Phe Glu Arg Asp Gly Met
210                 215                 220

Trp Leu Thr Ala Gly Glu Trp Gly Gly Pro Lys Lys Gly Glu Ile
225                 230                 235                 240

Val Thr Lys Thr Val Arg Tyr Arg Thr Val Gly Asp Met Ser Cys Thr
                245                 250                 255

Gly Ala Val Leu Ser Glu Ala Arg Thr Ile Asp Asp Val Ile Glu Glu
            260                 265                 270

Ile Ala Thr Ser Thr Leu Thr Glu Arg Gly Ala Thr Arg Ala Asp Asp
        275                 280                 285

Arg Leu Ser Glu Ser Ala Met Glu Asp Arg Lys Lys Glu Gly Tyr Phe
    290                 295                 300

<210> SEQ ID NO 3
<211> LENGTH: 433
<212> TYPE: PRT
<213> ORGANISM: Corynebacterium glutamicum

<400> SEQUENCE: 3

Met Thr Ala Pro Thr Leu Asn Lys Ala Ser Glu Lys Ile Ala Ser Arg
1               5                   10                  15

Glu Thr Leu Arg Leu Cys Thr Ala Gly Ser Val Asp Asp Gly Lys Ser
            20                  25                  30

Thr Phe Val Gly Arg Leu Leu His Asp Thr Lys Ser Val Leu Ala Asp
        35                  40                  45

Gln Leu Ala Ser Val Glu Arg Thr Ser Ala Asp Arg Gly Phe Glu Gly
    50                  55                  60

Leu Asp Leu Ser Leu Leu Val Asp Gly Leu Arg Ala Glu Arg Glu Gln
65                  70                  75                  80

Gly Ile Thr Ile Asp Val Ala Tyr Arg Tyr Phe Ala Thr Asp Lys Arg
                85                  90                  95

Thr Phe Ile Leu Ala Asp Thr Pro Gly His Val Gln Tyr Thr Arg Asn
            100                 105                 110

Thr Val Thr Gly Val Ser Thr Ser Gln Val Val Leu Leu Val Asp
        115                 120                 125

Ala Arg His Gly Val Val Glu Gln Thr Arg Arg His Leu Ser Val Ser
    130                 135                 140

Ala Leu Leu Gly Val Arg Thr Val Ile Leu Ala Val Asn Lys Ile Asp
145                 150                 155                 160

Leu Val Asp Tyr Ser Glu Glu Val Phe Arg Asn Ile Glu Lys Glu Phe
                165                 170                 175

Val Gly Leu Ala Ser Ala Leu Asp Val Thr Asp Thr His Val Val Pro
            180                 185                 190

Ile Ser Ala Leu Lys Gly Asp Asn Val Ala Glu Pro Ser Thr His Met
        195                 200                 205
```

-continued

```
Asp Trp Tyr Thr Gly Pro Thr Val Leu Glu Ile Leu Glu Asn Val Glu
    210                 215                 220

Val Ser His Gly Arg Ala His Asp Leu Gly Phe Arg Phe Pro Ile Gln
225                 230                 235                 240

Tyr Val Ile Arg Glu His Ala Thr Asp Tyr Arg Gly Tyr Ala Gly Thr
                245                 250                 255

Ile Asn Ala Gly Ser Val Ser Val Gly Asp Thr Val Tyr Leu Pro Glu
                260                 265                 270

Gly Arg Thr Thr Gln Val Thr His Ile Asp Ser Ala Asp Gly Ser Leu
            275                 280                 285

Gln Thr Ala Ser Val Gly Glu Ala Val Leu Arg Leu Ala Gln Glu
    290                 295                 300

Ile Asp Leu Ile Arg Gly Glu Leu Ile Ala Gly Glu Asp Arg Pro Glu
305                 310                 315                 320

Ser Val Arg Ser Phe Asn Ala Thr Val Gly Leu Ala Asp Arg Thr
                325                 330                 335

Ile Lys Pro Gly Ala Ala Val Lys Val Arg Tyr Gly Thr Glu Leu Val
                340                 345                 350

Arg Gly Arg Val Ala Ala Ile Glu Arg Val Leu Asp Ile Asp Gly Val
            355                 360                 365

Asn Asp Asn Glu Ala Pro Glu Thr Tyr Gly Leu Asn Asp Ile Ala His
    370                 375                 380

Val Arg Ile Asp Val Ala Gly Glu Leu Glu Val Glu Asp Tyr Ala Ala
385                 390                 395                 400

Arg Gly Ala Ile Gly Ser Phe Leu Leu Ile Asp Gln Ser Ser Gly Asp
                405                 410                 415

Thr Leu Ala Ala Gly Leu Val Gly His Arg Leu Arg Asn Asn Trp Ser
            420                 425                 430

Ile
```

```
<210> SEQ ID NO 4
<211> LENGTH: 2170
<212> TYPE: DNA
<213> ORGANISM: Corynebacterium glutamicum
<220> FEATURE:
<221> NAME/KEY: CDS
<222> LOCATION: (271)..(1203)
<223> OTHER INFORMATION:
<221> NAME/KEY: CDS
<222> LOCATION: (1392)..(1955)
<223> OTHER INFORMATION:

<400> SEQUENCE: 4
```

```
tccgacaacg gacttcttta aaagatgctt ttcgacgccg ctccccaacc attaaccccg      60
cgagaaatat tcatcgaata gatgtcgatc tacctgcaaa tacgctcggt ctacaaataa     120
tgaacagaac tgtctacttt tcaaactgct ttttgtgtag actcaagtca cagaggccac     180
ttcaagtaga tgtttcgtaa ttgtttacag cgtttacgca agcggtcgac caacaaaaac     240
agcacttcaa tgattggagc accaccccgac atg ggc aat gtg tac aac aac atc    294
                                    Met Gly Asn Val Tyr Asn Asn Ile
                                    1               5 acc gaa acc atc ggc cac acc cca ctg gta aag ctg aac aag ctc acc      342
Thr Glu Thr Ile Gly His Thr Pro Leu Val Lys Leu Asn Lys Leu Thr
        10                  15                  20 gaa ggc ctc gac gca act gtc ctg gtc aag ctt gag tca ttc aac cca      390
Glu Gly Leu Asp Ala Thr Val Leu Val Lys Leu Glu Ser Phe Asn Pro
25                  30                  35                  40
```

-continued

| | |
|---|---|
| gca aac tcc gtc aag gac cgt atc ggt ctg gcc atc gtt gaa gat gca<br>Ala Asn Ser Val Lys Asp Arg Ile Gly Leu Ala Ile Val Glu Asp Ala<br>                45                  50                55 | 438 |
| gag aag tcc ggt gca ctg aag cca ggc ggc acc atc gtt gaa gca acc<br>Glu Lys Ser Gly Ala Leu Lys Pro Gly Gly Thr Ile Val Glu Ala Thr<br>     60                 65                  70 | 486 |
| tcc ggc aac acc ggt atc gca ctg gca atg gtc ggc gct gca cgc gga<br>Ser Gly Asn Thr Gly Ile Ala Leu Ala Met Val Gly Ala Ala Arg Gly<br>         75                  80                85 | 534 |
| tac aac gtt gtt ctc acc atg ccg gag acc atg tcc aac gag cgt cgc<br>Tyr Asn Val Val Leu Thr Met Pro Glu Thr Met Ser Asn Glu Arg Arg<br>90                  95                100 | 582 |
| gtt ctc ctc cgc gct tac ggt gca gag atc gtt ctt acc cca ggt gca<br>Val Leu Leu Arg Ala Tyr Gly Ala Glu Ile Val Leu Thr Pro Gly Ala<br>105               110              115            120 | 630 |
| gca ggc atg cag ggt gca aag gac aag gca gac gaa atc gtc gct gaa<br>Ala Gly Met Gln Gly Ala Lys Asp Lys Ala Asp Glu Ile Val Ala Glu<br>                125              130            135 | 678 |
| cgc gaa aac gca gtc ctt gct cgc cag ttc gag aac gag gca aac cca<br>Arg Glu Asn Ala Val Leu Ala Arg Gln Phe Glu Asn Glu Ala Asn Pro<br>          140              145            150 | 726 |
| cgc gtc cac cgc gac acc acc gcg aag gaa atc ctc gaa gac acc gac<br>Arg Val His Arg Asp Thr Thr Ala Lys Glu Ile Leu Glu Asp Thr Asp<br>155               160              165 | 774 |
| ggc aac gtt gat atc ttc gtt gca agc ttc ggc acc ggc gga acc gtc<br>Gly Asn Val Asp Ile Phe Val Ala Ser Phe Gly Thr Gly Gly Thr Val<br>                170              175            180 | 822 |
| acc ggc gtt ggc cag gtc ctg aag gaa aac aac gca gac gta cag gtc<br>Thr Gly Val Gly Gln Val Leu Lys Glu Asn Asn Ala Asp Val Gln Val<br>185               190              195            200 | 870 |
| tac acc gtc gag cca gaa gcg tcc cca ctt ctg acc gct ggc aag gct<br>Tyr Thr Val Glu Pro Glu Ala Ser Pro Leu Leu Thr Ala Gly Lys Ala<br>                205              210            215 | 918 |
| ggt cca cac aag atc cag ggc atc ggc gca aac ttc atc ccc gag gtc<br>Gly Pro His Lys Ile Gln Gly Ile Gly Ala Asn Phe Ile Pro Glu Val<br>          220              225            230 | 966 |
| ctg gac cgc aag gtt ctc gac gac gtg ctg acc gtc tcc aac gaa gac<br>Leu Asp Arg Lys Val Leu Asp Asp Val Leu Thr Val Ser Asn Glu Asp<br>235               240              245 | 1014 |
| gca atc gca ttc tcc cgc aag ctc gct acc gaa gag ggc atc ctc ggc<br>Ala Ile Ala Phe Ser Arg Lys Leu Ala Thr Glu Glu Gly Ile Leu Gly<br>          250              255            260 | 1062 |
| ggt atc tcc acc ggc gca aac atc aag gca gct ctt gac ctt gca gca<br>Gly Ile Ser Thr Gly Ala Asn Ile Lys Ala Ala Leu Asp Leu Ala Ala<br>265               270              275            280 | 1110 |
| aag cca gag aac gct ggc aaa acc atc gtc acc gtt gtc acc gac ttc<br>Lys Pro Glu Asn Ala Gly Lys Thr Ile Val Thr Val Val Thr Asp Phe<br>                285              290            295 | 1158 |
| ggc gag cgc tac gtc tcc acc gtt ctt tac gaa gac atc cgc gac<br>Gly Glu Arg Tyr Val Ser Thr Val Leu Tyr Glu Asp Ile Arg Asp<br>          300              305            310 | 1203 |
| taattcttag cgactgttaa ccactcaagc tctttgcttg gtggttttt tcatgtctca | 1263 |
| aggtcgggtc gggtgcgatt cgggtcggtt ttgagtgtct ttgagtcctt ttaagtcctt | 1323 |
| ctttgcccgt gaataattct ctggatagtt tccacgtgca gttaagtcac gctgttagac | 1383 |
| ttgcctgc atg ctc tcg aca ata aaa atg atc cgt gaa gat ctc gca aac<br>         Met Leu Ser Thr Ile Lys Met Ile Arg Glu Asp Leu Ala Asn<br>                              315                320            325 | 1433 |
| gct cgt gaa cac gat cca gca gcc cga ggc gat tta gaa aac gca gtg | 1481 |

-continued

```
Ala Arg Glu His Asp Pro Ala Ala Arg Gly Asp Leu Glu Asn Ala Val
            330                 335                 340 gtt tac tcc gga ctc cac gcc atc tgg gca cat cga gtt gcc aac agc    1529
Val Tyr Ser Gly Leu His Ala Ile Trp Ala His Arg Val Ala Asn Ser
        345                 350                 355 tgg tgg aaa tcc ggt ttc cgc ggc ccc gcc cgc gta tta gcc caa ttc    1577
Trp Trp Lys Ser Gly Phe Arg Gly Pro Ala Arg Val Leu Ala Gln Phe
    360                 365                 370 acc cga ttc ctc acc ggc att gaa att cac ccc ggt gcc acc att ggt    1625
Thr Arg Phe Leu Thr Gly Ile Glu Ile His Pro Gly Ala Thr Ile Gly
375                 380                 385 cgt cgc ttt ttt att gac cac gga atg gga atc gtc atc ggc gaa acc    1673
Arg Arg Phe Phe Ile Asp His Gly Met Gly Ile Val Ile Gly Glu Thr
390                 395                 400                 405 gct gaa atc ggc gaa ggc gtc atg ctc tac cac ggc gtc acc ctc ggc    1721
Ala Glu Ile Gly Glu Gly Val Met Leu Tyr His Gly Val Thr Leu Gly
            410                 415                 420 gga cag gtt ctc acc caa acc aag cgc cac ccc acg ctc tgc gac aac    1769
Gly Gln Val Leu Thr Gln Thr Lys Arg His Pro Thr Leu Cys Asp Asn
        425                 430                 435 gtg aca gtc ggc gcg ggc gca aaa atc tta ggt ccc atc acc atc ggc    1817
Val Thr Val Gly Ala Gly Ala Lys Ile Leu Gly Pro Ile Thr Ile Gly
    440                 445                 450 gaa ggc tcc gca att ggc gcc aat gca gtt gtc acc aaa gac gtg ccg    1865
Glu Gly Ser Ala Ile Gly Ala Asn Ala Val Val Thr Lys Asp Val Pro
455                 460                 465 gca gaa cac atc gca gtc gga att cct gcg gta gca cgc cca cgt ggc    1913
Ala Glu His Ile Ala Val Gly Ile Pro Ala Val Ala Arg Pro Arg Gly
470                 475                 480                 485 aag aca gag aag atc aag ctc gtc gat ccg gac tat tac att            1955
Lys Thr Glu Lys Ile Lys Leu Val Asp Pro Asp Tyr Tyr Ile
            490                 495 taagaacagt tagcgcccta cctgaagttc aggcagggcg cttttttggg aagctccaga    2015
gtgcgtttgt tagccacgca ctagggacct ttaaccgtct aaaaccgccc ctgtgcgctt    2075
ctcagcacta cccgtgagaa ccaccccccct gtgccagcta gttctttaga tccttatact    2135
cagggttctt ctgaatgaag ccagcgactg cagag                                2170
```

<210> SEQ ID NO 5
<211> LENGTH: 311
<212> TYPE: PRT
<213> ORGANISM: Corynebacterium glutamicum

<400> SEQUENCE: 5

```
Met Gly Asn Val Tyr Asn Asn Ile Thr Glu Thr Ile Gly His Thr Pro
1               5                   10                  15

Leu Val Lys Leu Asn Lys Leu Thr Glu Gly Leu Asp Ala Thr Val Leu
            20                  25                  30

Val Lys Leu Glu Ser Phe Asn Pro Ala Asn Ser Val Lys Asp Arg Ile
        35                  40                  45

Gly Leu Ala Ile Val Glu Asp Ala Glu Lys Ser Gly Ala Leu Lys Pro
    50                  55                  60

Gly Gly Thr Ile Val Glu Ala Thr Ser Gly Asn Thr Gly Ile Ala Leu
65                  70                  75                  80

Ala Met Val Gly Ala Ala Arg Gly Tyr Asn Val Val Leu Thr Met Pro
                85                  90                  95

Glu Thr Met Ser Asn Glu Arg Arg Val Leu Leu Arg Ala Tyr Gly Ala
            100                 105                 110
```

-continued

Glu Ile Val Leu Thr Pro Gly Ala Gly Met Gln Gly Ala Lys Asp
            115                 120                 125

Lys Ala Asp Glu Ile Val Ala Glu Arg Glu Asn Ala Val Leu Ala Arg
130                 135                 140

Gln Phe Glu Asn Glu Ala Asn Pro Arg Val His Arg Asp Thr Thr Ala
145                 150                 155                 160

Lys Glu Ile Leu Glu Asp Thr Asp Gly Asn Val Asp Ile Phe Val Ala
                165                 170                 175

Ser Phe Gly Thr Gly Thr Val Thr Gly Val Gly Gln Val Leu Lys
            180                 185                 190

Glu Asn Asn Ala Asp Val Gln Val Tyr Thr Val Glu Pro Glu Ala Ser
            195                 200                 205

Pro Leu Leu Thr Ala Gly Lys Ala Gly Pro His Lys Ile Gln Gly Ile
210                 215                 220

Gly Ala Asn Phe Ile Pro Glu Val Leu Asp Arg Lys Val Leu Asp Asp
225                 230                 235                 240

Val Leu Thr Val Ser Asn Glu Asp Ala Ile Ala Phe Ser Arg Lys Leu
                245                 250                 255

Ala Thr Glu Glu Gly Ile Leu Gly Gly Ile Ser Thr Gly Ala Asn Ile
            260                 265                 270

Lys Ala Ala Leu Asp Leu Ala Ala Lys Pro Glu Asn Ala Gly Lys Thr
            275                 280                 285

Ile Val Thr Val Val Thr Asp Phe Gly Glu Arg Tyr Val Ser Thr Val
            290                 295                 300

Leu Tyr Glu Asp Ile Arg Asp
305                 310

<210> SEQ ID NO 6
<211> LENGTH: 188
<212> TYPE: PRT
<213> ORGANISM: Corynebacterium glutamicum

<400> SEQUENCE: 6

Met Leu Ser Thr Ile Lys Met Ile Arg Glu Asp Leu Ala Asn Ala Arg
1               5                   10                  15

Glu His Asp Pro Ala Ala Arg Gly Asp Leu Glu Asn Ala Val Val Tyr
            20                  25                  30

Ser Gly Leu His Ala Ile Trp Ala His Arg Val Ala Asn Ser Trp Trp
        35                  40                  45

Lys Ser Gly Phe Arg Gly Pro Ala Arg Val Leu Ala Gln Phe Thr Arg
    50                  55                  60

Phe Leu Thr Gly Ile Glu Ile His Pro Gly Ala Thr Ile Gly Arg Arg
65                  70                  75                  80

Phe Phe Ile Asp His Gly Met Gly Ile Val Ile Gly Glu Thr Ala Glu
                85                  90                  95

Ile Gly Glu Gly Val Met Leu Tyr His Gly Val Thr Leu Gly Gly Gln
            100                 105                 110

Val Leu Thr Gln Thr Lys Arg His Pro Thr Leu Cys Asp Asn Val Thr
        115                 120                 125

Val Gly Ala Gly Ala Lys Ile Leu Gly Pro Ile Thr Ile Gly Glu Gly
    130                 135                 140

Ser Ala Ile Gly Ala Asn Ala Val Val Thr Lys Asp Val Pro Ala Glu
145                 150                 155                 160

His Ile Ala Val Gly Ile Pro Ala Val Ala Arg Pro Arg Gly Lys Thr
                165                 170                 175

-continued

```
Glu Lys Ile Lys Leu Val Asp Pro Asp Tyr Tyr Ile
            180                 185

<210> SEQ ID NO 7
<211> LENGTH: 1240
<212> TYPE: DNA
<213> ORGANISM: Corynebacterium glutamicum
<220> FEATURE:
<221> NAME/KEY: CDS
<222> LOCATION: (250)..(1032)
<223> OTHER INFORMATION:

<400> SEQUENCE: 7
tggtgtgagt cttcggagga aacccaatcc caaccgcaac caccctctgt actgcccata      60
ctgcgcggga gaagttcttt tccccgatga gcaaacagaa ttcgcgtggt tgtgtgcgga     120
ttgcaccaga gttttttgaag tgaaatatca cggccaggac gatccagtgc acaggccagc    180
accagcaaag tccacatcgc aagcattaaa agaatctctc gaaagacaca aaagaggtga    240 gtcgcaaca atg agc ttt caa cta gtt aac gcc ctg aaa aat act ggt tcg    291
          Met Ser Phe Gln Leu Val Asn Ala Leu Lys Asn Thr Gly Ser
            1               5                  10 gta aaa gat ccc gag atc tca ccc gaa gga cct cgc acg acc aca ccg      339
Val Lys Asp Pro Glu Ile Ser Pro Glu Gly Pro Arg Thr Thr Thr Pro
15              20                  25                  30 ttg tca cca gag gta gca aaa cat aac gag gaa ctc gtc gaa aag cat      387
Leu Ser Pro Glu Val Ala Lys His Asn Glu Glu Leu Val Glu Lys His
                35                  40                  45 gct gct gcg ttg tat gac gcc agc gcg caa gag atc ctg gaa tgg aca      435
Ala Ala Ala Leu Tyr Asp Ala Ser Ala Gln Glu Ile Leu Glu Trp Thr
            50                  55                  60 gcc gag cac gcg ccg ggc gct att gca gtg acc ttg agc atg gaa aac      483
Ala Glu His Ala Pro Gly Ala Ile Ala Val Thr Leu Ser Met Glu Asn
65              70                  75 acc gtg ctg gcg gag ctg gct gcg cgg cac ctg ccg gaa gct gat ttc      531
Thr Val Leu Ala Glu Leu Ala Ala Arg His Leu Pro Glu Ala Asp Phe
            80                  85                  90 ctc ttt ttg gac acc ggt tac cac ttc aag gag acc ctt gaa gtt gcc      579
Leu Phe Leu Asp Thr Gly Tyr His Phe Lys Glu Thr Leu Glu Val Ala
95                  100                 105                 110 cgt cag gta gat gag cgc tat tcc cag aag ctt gtc acc gcg ctg ccg      627
Arg Gln Val Asp Glu Arg Tyr Ser Gln Lys Leu Val Thr Ala Leu Pro
                115                 120                 125 atc ctc aag cgc acg gag cag gat tcc att tat ggt ctc aac ctg tac      675
Ile Leu Lys Arg Thr Glu Gln Asp Ser Ile Tyr Gly Leu Asn Leu Tyr
            130                 135                 140 cgc agc aac cca gcg gcg tgc tgc cga atg cgc aaa gtt gaa ccg ctg      723
Arg Ser Asn Pro Ala Ala Cys Cys Arg Met Arg Lys Val Glu Pro Leu
145                 150                 155 gcg gcg tcg tta agc cca tac gct ggc tgg atc acc ggc ctg cgc cgc      771
Ala Ala Ser Leu Ser Pro Tyr Ala Gly Trp Ile Thr Gly Leu Arg Arg
                160                 165                 170 gct gat ggc cca acc cgt gct caa gcc cct gcg ctg agc ttg gat gcc      819
Ala Asp Gly Pro Thr Arg Ala Gln Ala Pro Ala Leu Ser Leu Asp Ala
175                 180                 185                 190 acc gga agg ctc aag att tct cca att atc acc tgg tca ttg gag gaa      867
Thr Gly Arg Leu Lys Ile Ser Pro Ile Ile Thr Trp Ser Leu Glu Glu
                195                 200                 205 acc aac gag ttc att gcg gac aac aac ctc atc gat cac cca ctt acc      915
Thr Asn Glu Phe Ile Ala Asp Asn Asn Leu Ile Asp His Pro Leu Thr
            210                 215                 220
```

```
cat cag ggt tat cca tca att gga tgc gaa acc tgc acc ctt cct gtt      963
His Gln Gly Tyr Pro Ser Ile Gly Cys Glu Thr Cys Thr Leu Pro Val
        225                 230                 235 gct gaa gga caa gac cct agg gcc ggc cgt tgg gct gga aac gcc aag     1011
Ala Glu Gly Gln Asp Pro Arg Ala Gly Arg Trp Ala Gly Asn Ala Lys
240                 245                 250 aca gaa tgc gga ctt cac tca tgaccacaac cgttgcatca gtactatccc        1062
Thr Glu Cys Gly Leu His Ser
255                 260 cacaccttaa agatcttgaa aatgaatcca tccacatcct ccgcgaggta gctggccagt   1122
ttgataaggt cggcctgctg ttttccggcg gtaaggattc cgtcgtggtg tacgagcttg   1182
cgcgccgcgc tttcgctcca gctaacgtgc cttttgaatt gctgcacgtg gacaccgg    1240
```

<210> SEQ ID NO 8
<211> LENGTH: 261
<212> TYPE: PRT
<213> ORGANISM: Corynebacterium glutamicum

<400> SEQUENCE: 8

```
Met Ser Phe Gln Leu Val Asn Ala Leu Lys Asn Thr Gly Ser Val Lys
1               5                   10                  15

Asp Pro Glu Ile Ser Pro Glu Gly Pro Arg Thr Thr Thr Pro Leu Ser
            20                  25                  30

Pro Glu Val Ala Lys His Asn Glu Glu Leu Val Glu Lys His Ala Ala
        35                  40                  45

Ala Leu Tyr Asp Ala Ser Ala Gln Glu Ile Leu Glu Trp Thr Ala Glu
    50                  55                  60

His Ala Pro Gly Ala Ile Ala Val Thr Leu Ser Met Glu Asn Thr Val
65                  70                  75                  80

Leu Ala Glu Leu Ala Ala Arg His Leu Pro Glu Ala Asp Phe Leu Phe
                85                  90                  95

Leu Asp Thr Gly Tyr His Phe Lys Glu Thr Leu Glu Val Ala Arg Gln
            100                 105                 110

Val Asp Glu Arg Tyr Ser Gln Lys Leu Val Thr Ala Leu Pro Ile Leu
        115                 120                 125

Lys Arg Thr Glu Gln Asp Ser Ile Tyr Gly Leu Asn Leu Tyr Arg Ser
    130                 135                 140

Asn Pro Ala Ala Cys Cys Arg Met Arg Lys Val Glu Pro Leu Ala Ala
145                 150                 155                 160

Ser Leu Ser Pro Tyr Ala Gly Trp Ile Thr Gly Leu Arg Arg Ala Asp
                165                 170                 175

Gly Pro Thr Arg Ala Gln Ala Pro Ala Leu Ser Leu Asp Ala Thr Gly
            180                 185                 190

Arg Leu Lys Ile Ser Pro Ile Ile Thr Trp Ser Leu Glu Glu Thr Asn
        195                 200                 205

Glu Phe Ile Ala Asp Asn Asn Leu Ile Asp His Pro Leu Thr His Gln
    210                 215                 220

Gly Tyr Pro Ser Ile Gly Cys Glu Thr Cys Thr Leu Pro Val Ala Glu
225                 230                 235                 240

Gly Gln Asp Pro Arg Ala Gly Arg Trp Ala Gly Asn Ala Lys Thr Glu
                245                 250                 255

Cys Gly Leu His Ser
            260
```

<210> SEQ ID NO 9

```
<211> LENGTH: 28
<212> TYPE: DNA
<213> ORGANISM: Artificial Sequence
<220> FEATURE:
<223> OTHER INFORMATION: Synthetic DNA

<400> SEQUENCE: 9
ctggtaccgc ggacttcact catgacca                              28

<210> SEQ ID NO 10
<211> LENGTH: 28
<212> TYPE: DNA
<213> ORGANISM: Artificial Sequence
<220> FEATURE:
<223> OTHER INFORMATION: Synthetic DNA

<400> SEQUENCE: 10
cgtctagagg aacctgcggt gcacagac                              28

<210> SEQ ID NO 11
<211> LENGTH: 28
<212> TYPE: DNA
<213> ORGANISM: Artificial Sequence
<220> FEATURE:
<223> OTHER INFORMATION: Synthetic DNA

<400> SEQUENCE: 11
ctggtacctc acgctgttag acttgcct                              28

<210> SEQ ID NO 12
<211> LENGTH: 28
<212> TYPE: DNA
<213> ORGANISM: Artificial Sequence
<220> FEATURE:
<223> OTHER INFORMATION: Synthetic DNA

<400> SEQUENCE: 12
gatctagaac aaacgcactc tggagctt                              28

<210> SEQ ID NO 13
<211> LENGTH: 28
<212> TYPE: DNA
<213> ORGANISM: Artificial Sequence
<220> FEATURE:
<223> OTHER INFORMATION: Synthetic DNA

<400> SEQUENCE: 13
acggtacctg agtcgcaaca atgagctt                              28

<210> SEQ ID NO 14
<211> LENGTH: 28
<212> TYPE: DNA
<213> ORGANISM: Artificial Sequence
<220> FEATURE:
<223> OTHER INFORMATION: Synthetic DNA

<400> SEQUENCE: 14
gttctagacg gaggatgtgg atggattc                              28

<210> SEQ ID NO 15
<211> LENGTH: 28
<212> TYPE: DNA
<213> ORGANISM: Artificial Sequence
<220> FEATURE:
<223> OTHER INFORMATION: Synthetic DNA

<400> SEQUENCE: 15
```

```
agggtaccca agcggtcgac caacaaaa                                              28

<210> SEQ ID NO 16
<211> LENGTH: 28
<212> TYPE: DNA
<213> ORGANISM: Artificial Sequence
<220> FEATURE:
<223> OTHER INFORMATION: Synthetic DNA

<400> SEQUENCE: 16
cttctagaat tagtcgcgga tgtcttcg                                              28
```